(12) United States Patent
Chance et al.

(10) Patent No.: US 6,957,094 B2
(45) Date of Patent: *Oct. 18, 2005

(54) EXAMINATION OF SCATTERING PROPERTIES OF BIOLOGICAL TISSUE

(75) Inventors: Britton Chance, Marathon, FL (US); Hanli Liu, Arlington, TX (US)

(73) Assignee: Non-Invasive Technology, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/299,598

(22) Filed: Nov. 19, 2002

(65) Prior Publication Data

US 2003/0166997 A1 Sep. 4, 2003

Related U.S. Application Data

(63) Continuation of application No. 08/849,203, filed as application No. PCT/US95/15666 on Dec. 4, 1995, now Pat. No. 6,493,565, which is a continuation-in-part of application No. 08/349,839, filed on Dec. 2, 1994, now Pat. No. 5,782,755.

(51) Int. Cl.[7] .............................................. A61B 5/00
(52) U.S. Cl. ...................... 600/310; 600/314; 600/316; 600/473; 600/476
(58) Field of Search ................................ 600/310, 316, 600/322, 473, 476, 314

(56) References Cited

U.S. PATENT DOCUMENTS

| | | | |
|---|---|---|---|
| 4,014,321 A | 3/1977 | March | |
| 4,029,085 A | 6/1977 | DeWitt et al. | |
| 4,223,680 A | 9/1980 | Jobsis | |
| 4,281,645 A | 8/1981 | Jobsis | |
| 4,321,930 A | 3/1982 | Jobsis et al. | |
| 4,576,173 A | 3/1986 | Parker et al. | |
| 4,655,225 A | 4/1987 | Dahne et al. | |
| 4,700,708 A | 10/1987 | New, Jr. et al. | |

(Continued)

FOREIGN PATENT DOCUMENTS

| | | |
|---|---|---|
| DE | 25 38 985 | 5/1976 |
| DE | 43 37 570 | 5/1995 |
| DE | 44 17 639 | 11/1995 |
| EP | 0 102 816 | 3/1984 |
| EP | 0 404 562 | 12/1990 |
| WO | WO 92/20273 | 11/1992 |
| WO | WO 96/16592 | 6/1996 |

OTHER PUBLICATIONS

Haida et al., "A New Method to Estimate the Ratio of Absorption Coefficients of Two Wave Lengths Using Phase Modulating NIR Spectroscopy," abstract submitted to ISOTT in Mainz, Germany, 1992.

(Continued)

*Primary Examiner*—Eric F. Winakur
(74) *Attorney, Agent, or Firm*—Ivan David Zitkovsky

(57) ABSTRACT

This invention is a scheme for monitoring a solute in a biological system comprising the steps of delivering light into a biological system (12) containing a solute, the light having a wavelength selected to be in a range wherein the solute is substantially non-absorbing; detecting at least first and second portions of the delivered light, the first portion having traveled through the biological system along one or more paths characterized by a first average path length, and the second portion having traveled through the biological system along one or more paths characterized by a second average path length that is greater than the first average path length; and comparing the first and second portions of the delivered light to monitor concentration of the solute in the biological system. Also described are schemes for monitoring low molecular weight polyhydroxy solutes, generally sugars (mannitol, fructose, sucrose, glucose, sorbitol), alcohols (methanol, ethanol, propanediol), and electrolytes (sodium, potassium, magnesium, calcium, and chloride ions).

24 Claims, 22 Drawing Sheets

U.S. PATENT DOCUMENTS

| | | |
|---|---|---|
| 4,714,341 A | 12/1987 | Hamaguri et al. |
| 4,773,422 A | 9/1988 | Isaacson et al. |
| 4,800,495 A | 1/1989 | Smith |
| 4,800,885 A | 1/1989 | Johnson |
| 4,836,207 A | 6/1989 | Bursell et al. |
| 4,846,183 A | 7/1989 | Martin |
| 4,869,254 A | 9/1989 | Stone et al. |
| 4,880,304 A | 11/1989 | Jaeb et al. |
| 4,908,762 A | 3/1990 | Suzuki et al. |
| 4,926,867 A | 5/1990 | Kanda et al. |
| 4,972,331 A | 11/1990 | Chance |
| 5,057,695 A | 10/1991 | Hirao et al. |
| 5,119,815 A | 6/1992 | Chance |
| 5,137,355 A | 8/1992 | Barbour et al. |
| 5,178,142 A | 1/1993 | Harjunmaa et al. |
| 5,190,039 A | 3/1993 | Takeuchi et al. |
| 5,277,181 A | 1/1994 | Mendelson et al. |
| 5,497,769 A | 3/1996 | Gratton et al. |
| 5,544,651 A | 8/1996 | Wilk |
| 5,551,422 A | 9/1996 | Simonsen et al. |
| 5,782,755 A | 7/1998 | Chance et al. |
| 5,845,639 A | 12/1998 | Hochman et al. |
| 5,853,370 A | 12/1998 | Chance et al. |

OTHER PUBLICATIONS

Haida et al., "A New Method to Estimate the Ratio of Absorption Coefficients of Two Wavelengths Using Phase-Modulated Near Infrared Light Spectroscopy," *Analytical Biochemistry*, 208:348–351. 1993.

Haida et al., "A New Method to Estimate the Ratio of Absorption Coefficients of Two Wavelengths Using Phase Modulated Near Infrared Light Spectroscopy," *Adv. Exp. Biol. and Med.*, 345:829–835, 1994.

Patterson et al., "Time resolved reflectance and transmittance for the non-invasive measurement of tissue optical properties," *Applied Optics*, 28(12):2331–2336.

Sevick et al., "Quantitation of Time- and Frequency-Resolved Optical Spectra for the Determination of Tissue Oxygenation." Analytical Biochemistry. 195:330–351. 1991.

| concentration of intralipid(%) | 0.1 | 0.6 | 1 | 1.3 | 1.5 |
|---|---|---|---|---|---|
| slope/glucose(e-4OD/mM/cm) | -0.27 | -1.02 | -1.56 | -1.88 | -2.05 |
| SD | 0.0037 | 0.014 | 0.037 | 0.088 | 0.071 |
| slope/glucose/%IL(e40D/mM/cm/%IL) | -2.7 | -1.7 | 1.56 | -1.45 | -1.37 |
| interc pt/glucose(e-4OD/mM) | 0.98 | 0.29 | 0.91 | 1.94 | 3.7 |
| SD | 0.15 | 0.083 | 0.09 | 0.36 | 0.27 |

FIG. 6

| | yeast=1.4% | | | yeast=2.8% | | 1%IL+1.4%yeast |
|---|---|---|---|---|---|---|
| scatterer | | | | | | |
| solute | mannitol | CH3OH* | NaCl | MOPS | water 27% | KCl | mannitol |
| solute conc. range(M) | 0.2 | 4.5 | 3.9 | 0.21 | | 1.74 | 0.4 |
| slope(e-4OD/mM/cm) | -1.11 | -0.052 | -0.16 | -1.25 | -0.033 | -0.55 | -1.77 |
| S.D. | 0.085 | 0.0072 | 0.0065 | 0.11 | 0.0014 | 0.038 | 0.036 |
| Intercept(e-4OD/mM) | 1.40 | 0.12 | 0.26 | 1.73 | 0.038 | 0.73 | 1.58 |
| S.D. | 0.17 | 0.048 | 0.0023 | 0.13 | 0.0013 | 0.036 | 0.13 |

* corrected for dilution

FIG. 10

| | IL=0.6% | | | IL=1% | |
|---|---|---|---|---|---|
| scatterer | | | | | |
| solut | mannitol | fructose | propanediol* | water 27% | NaCl |
| solute conc. range(M) | 0.18 | 0.12 | 1.24 | | 6.3 |
| slope(e-4OD/mM/cm) | -1.03 | -1.27 | -0.25 | -0.038 | -0.29 |
| S.D. | 0.019 | 0.042 | 0.023 | 0.0013 | 0.021 |
| intercept(e-4OD/mM) | 0.44 | 0.92 | 0.03 | 0.024 | 0.1 |
| S.D. | 0.063 | 0.12 | 0.004 | 0.0019 | 0.011 |

*corrected for dilution

FIG. 11

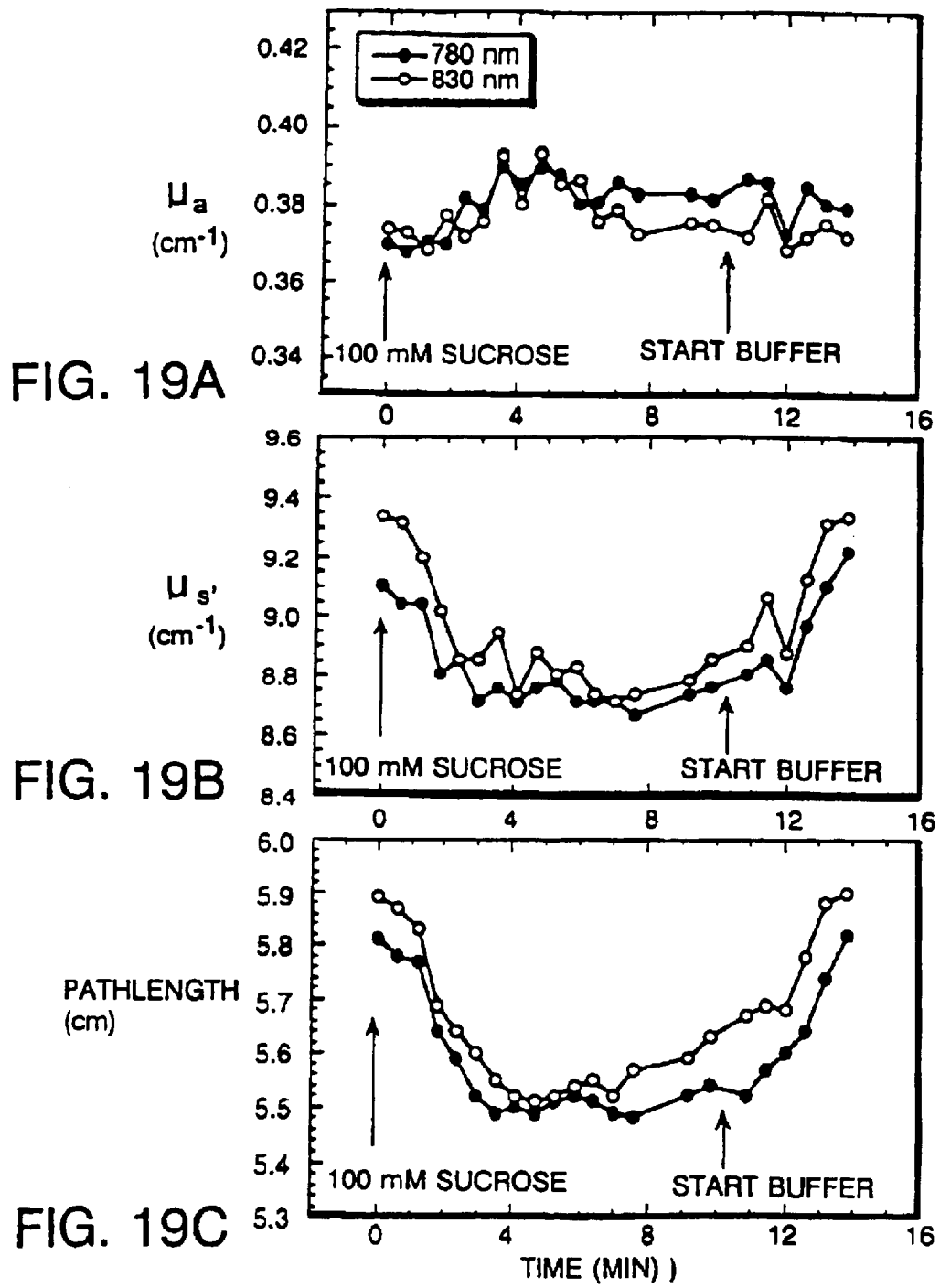

EXAMINATION OF SCATTERING PROPERTIES OF BIOLOGICAL TISSUE

This application is a continuation of U.S. application Ser. No. 08/849,203, filed on Nov. 17, 1997, now U.S. Pat. No. 6,493,565, which is a 371 of PCT/US95/15666 filed Dec. 4, 1995 which is a continuation-in-part of U.S. application Ser. No. 08/349,839 filed Dec. 2, 1994, now U.S. Pat. No. 5,782,755, which are incorporated by reference.

BACKGROUND

This invention relates to in vivo monitoring one or more solutes in a biological system using optical techniques.

Monitoring the concentration of a solute (e.g., low molecular weight carbohydrate or polyhydroxy compounds such as sugars (mannitol, sorbitol, fructose, sucrose, or glucose), alcohols (methanol, ethanol, or propanediol), and electrolytes (sodium, potassium, magnesium, calcium, or chloride ions)) in a biological system has important applications in the medical field. For example, it is important for diabetics, who have gone off insulin, to monitor their glucose level so that can remedy any serious deviation in the level before harm occurs.

Near infra-red radiation (NIR) has been used to study non-invasively the oxygen metabolism in tissue (for example, the brain, finger, or ear lobe). Using visible, NIR and infra-red (IR) radiation for medical imaging could bring several advantages. In the NIR or IR range the contrast factor between a tumor and a tissue is much larger than in the X-ray range. In addition, the visible to IR radiation is preferred over the X-ray radiation since it is non-ionizing; thus, it potentially causes fewer side effects. However, with lower energy radiation, such as visible or infra-red radiation, the radiation is strongly scattered and absorbed in biological tissue, and the migration path cannot be approximated by a straight line, making inapplicable certain aspects of cross-sectional imaging techniques.

SUMMARY

In a general aspect, the invention features a scheme for monitoring one (or more) solute in a biological system comprising the steps of: delivering light into a biological system containing one (or more) solute, the light having a wavelength selected to be in a range wherein the one (or more) solute is substantially non-absorbing; detecting at least first and second portions of the delivered light, the first portion having traveled through the biological system along one or more paths characterized by a first average path length, and the second portion having traveled through the biological system along one or more paths characterized by a second average path length that is greater than the first average path length; and comparing the first and second portions of the delivered light to monitor concentration of the one (or more) solute in the biological system.

Embodiments of the invention may include one or more of the following features. Comparing the first and second portions of the delivered light preferably comprises obtaining a characterization of the biological system based on a linear model relating an optical characteristic of the biological system and the first and second average path lengths. The characterization that is obtained may be the slope and/or the intercept of a line determined by fitting to the linear model measured characteristics of the first and second portions of light and distances representative of the first and second path lengths. Obtaining a characterization may comprise obtaining measures of first and second optical densities of the biological system based on the first and second portions of detected light and fitting the measures of optical densities to the generally linear model. Comparing the first and second portions of the delivered light may comprise determining a measure of the concentration of one or more of the solutes based on a comparison of the characterization of the biological system against a predetermined scale.

The monitoring scheme may further comprise determining a measure of a concentration of one or more of the solutes in the biological system based on a predetermined concentration scale. Detecting the first and second portions of the delivered light preferably comprises measuring first and second intensities ($I_1$, $I_2$) corresponding to the intensities of the first and second portions of light, respectively.

The monitoring scheme may further comprise determining changes, over time, in the first and second intensities ($I_1$, $I_2$) relative to first and second reference intensities ($I_{1,ref}$, $I_{2,ref}$). Determining relative changes in the first and second intensities may further comprise respectively determining first and second optical densities ($OD_1$, $OD_2$):

$$OD_1 = \log\left(\frac{I_1}{I_{1,ref}}\right)$$

$$OD_2 = \log\left(\frac{I_2}{I_{2,ref}}\right).$$

Comparing the first and second portions of the delivered light may comprise using a linear model relating the first and second optical densities to distances ($\rho_1$, $\rho_2$) representative of the first and second average path lengths to obtain a characterization of the biological system representative of the concentration of one or more of the solutes in the biological system. The characterization that is obtained is a slope (m) may be determined by $$m = \frac{OD_2 - OD_1}{\rho_2 - \rho_1}.$$

The characterization that is obtained may be an intercept (b) determined by $$b = \frac{OD_1 \cdot \rho_2 - OD_2 \cdot \rho_1}{\rho_2 - \rho_1}.$$

The monitoring scheme may further comprise detecting a third portion of the delivered light, the third portion having traveled through the biological system along one or more paths characterized by a third average path length that is greater than the first and second average path lengths.

In another aspect, the invention features a system for monitoring one or more solutes in a biological system comprising: at least two sources of light having a wavelength selected to be in a range wherein at least one of the one or more solutes is substantially non-absorbing, a detector positioned at different distances with respect to the at least two detectors to detect at least first and second portions of the delivered light, the first portion having traveled through the biological system along one or more paths characterized by a first average path length, and the second portion having traveled through the biological system along one or more paths characterized by a second average path length that is greater than the first average path length, and a comparator adapted to compare the first and second portions of the delivered light to monitor a concentration of one or more of the solutes in the biological system.

In one embodiment of the invention, two or more continuous light sources are used and light reflectance at separated input-output distances are measured. Approximation of the exact solution for the spatially resolved reflectance at separations larger than 2.5 cm provides a linear relationship between the separation and absorbance variation with respect to a reference sample. Slope and intercept of this straight line are functions of the absorption and scattering coefficients ($\mu_a$ and $\mu_s'$) of the measured sample. Using this technique, high measurement sensitivities for solute concentrations in a biological system can be achieved. For example, absorbency changes of approximately 0.2 milli OD are obtained for a 1 millimolar concentration change of the solute and per 1% change of the intralipid concentration.

Solutes contained in a biological system respond to migrating near-infrared and infrared light by acting primarily to scatter the applied light. The signal intensity of such migrating light is affected to a greater extent the longer the average path length migrated by the detected light. This enables us to obtain a linear relationship between an optical parameter of the biological system and at least two distances representative of average path lengths traveled by the detected light through the biological system (e.g., at least two different source detector spacing).

Solutes include low molecular weight carbohydrates such as sucrose, glucose, mannitol, sorbitol, inositol, maltose, lactose, galactose, and glucuronic acid; and hydroxy-functionalized compounds such as alcohols (methanol, ethanol), phenols, catechols, and flavanoids (e.g., flavanones, flavones); and metabolites and metabolic precursors thereof. Solutes also include neurotransmitters such as amino acids (γ-aminobutyric acid, glycine, glutamate), choline, acetylcholine, norepinephrine, epinephrine, dopamine, serotonin, and histamines; and electrolytes (sodium, potassium, magnesium, calcium) and other soluble ions of the IA, IIA, and VIIB groups of the periodic table. Solutes are present in the interstitial spaces between cells, present within cells, or present in the blood (e.g., soluble in serum), or a combination thereof. They may be released from or taken up by cells as intra- or inter-cellular messengers, as metabolites (or byproducts), or as metabolic precursors or nutrients.

Solutes may be labelled with one or more radioisotopes of H, C, O, S, or P (e.g., $^{32}P$ and tritium) or with a detectable agent (e.g., a contrast agent sensitive to a selected wavelength in the visible or infra-red range); or derivatized (e.g., deoxyglucose, or phosphoinositol). Solutes may thus be covalently linked to exogenous contrast agents; when linked to a detectable agent, either the solute or the agent may be measured or monitored according to the methods disclosed herein. For example, a wavelength may be selected such that a contrast agent is substantially non-absorbing, or a solute is substantially non-absorbing, or both.

Other features and advantages will become apparent from the following description and from the claims.

DESCRIPTION

FIG. 6 is a table indicating the optical effect of intralipid concentration upon glucose in the concentration range of 160 mM.

FIG. 10 is a table of baker's yeast as a scatterer and various solutes.

FIG. 11 is a table indicating the optical effect of a variety of solutes.

Figure 13A:
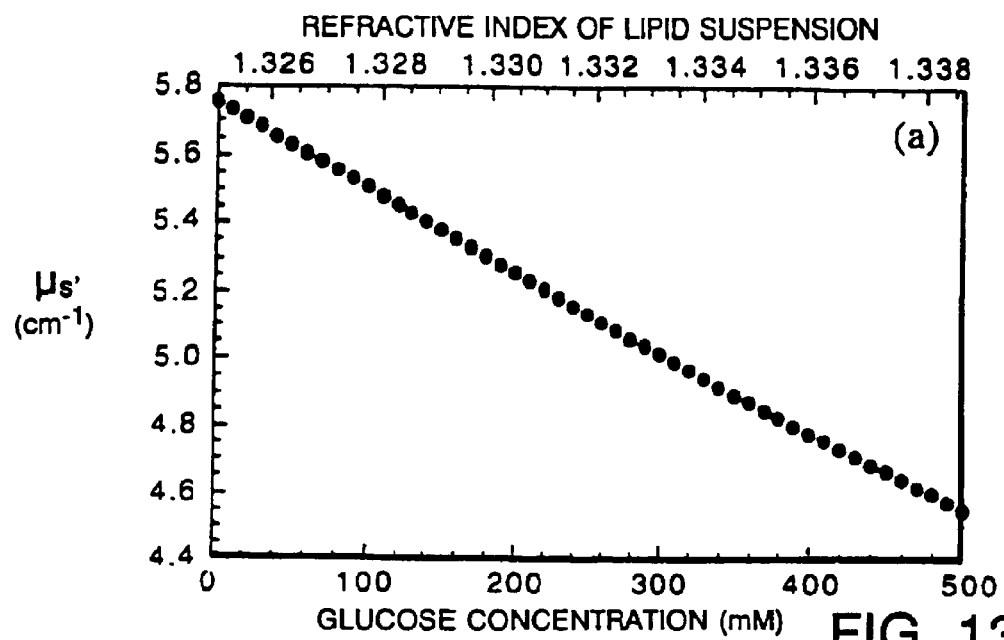
Figure 13B:
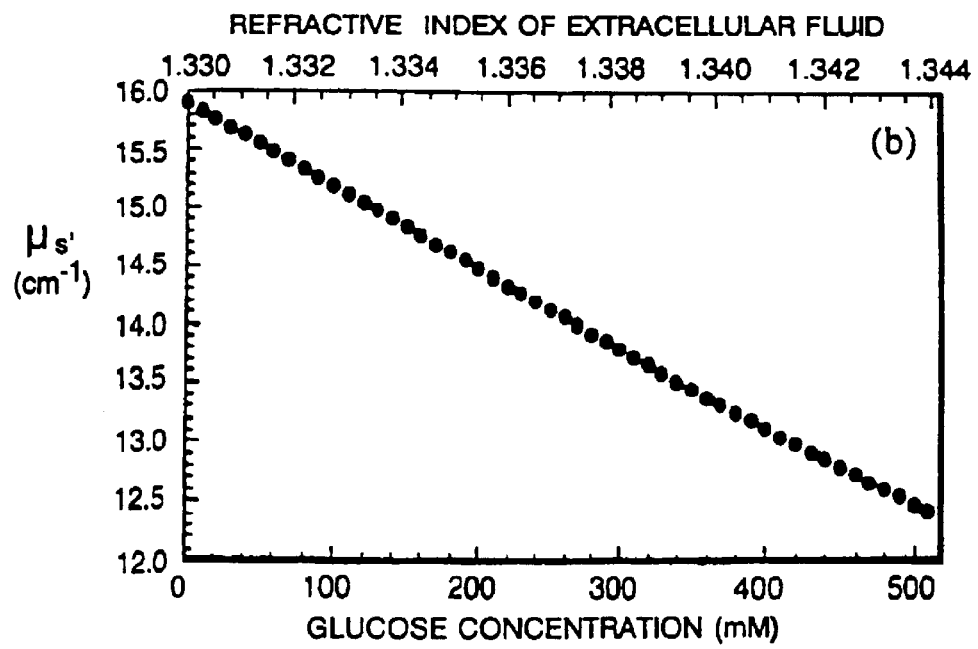

FIGS. 13(a)–(b) are a simulation of the reduced scattering coefficient, $\mu_s'$, for a 0.5% Intralipid-glucose suspension (a) and a perfused liver (b).

Figure 14A:
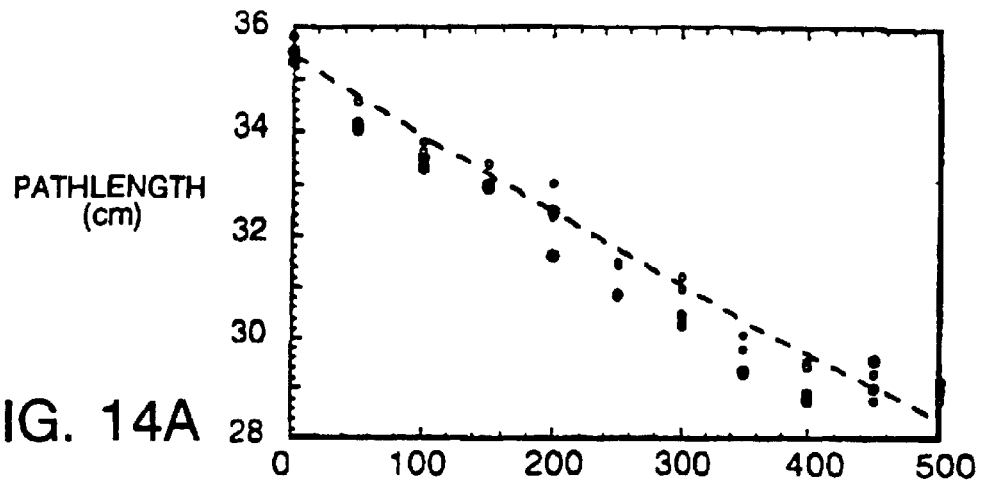
Figure 14B:
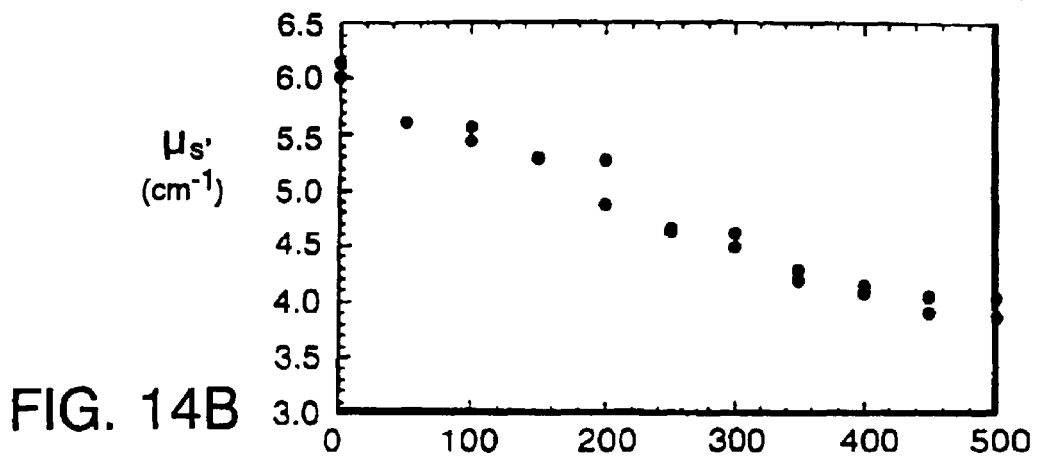
Figure 14C:
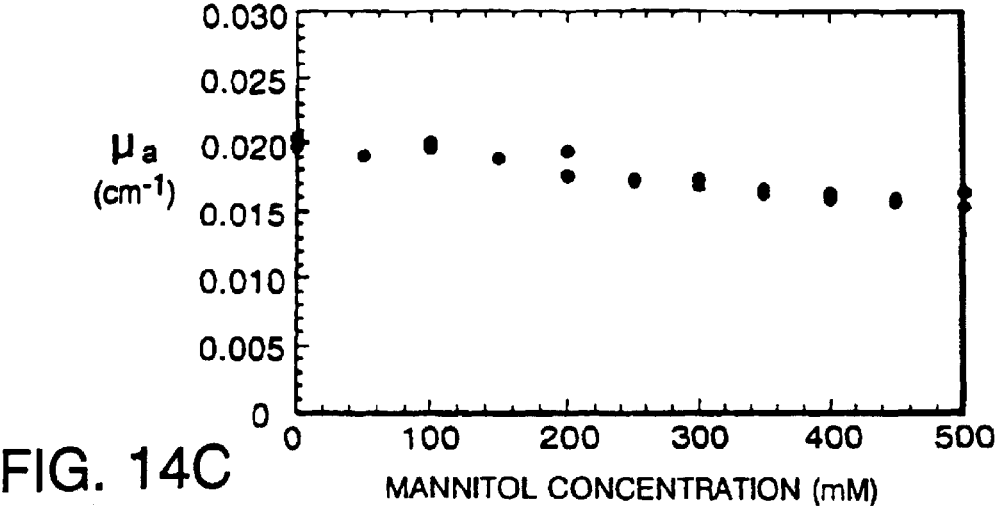

FIGS. 14(a)–(c) are plots of time-domain experimental results of a 0.5% Intralipid-mannitol suspension measured at 830 nm.

Figure 15A:
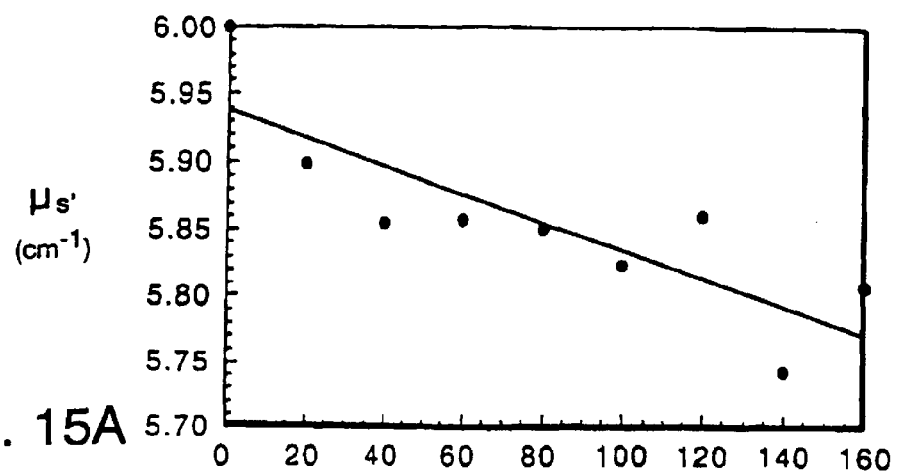
Figure 15B:
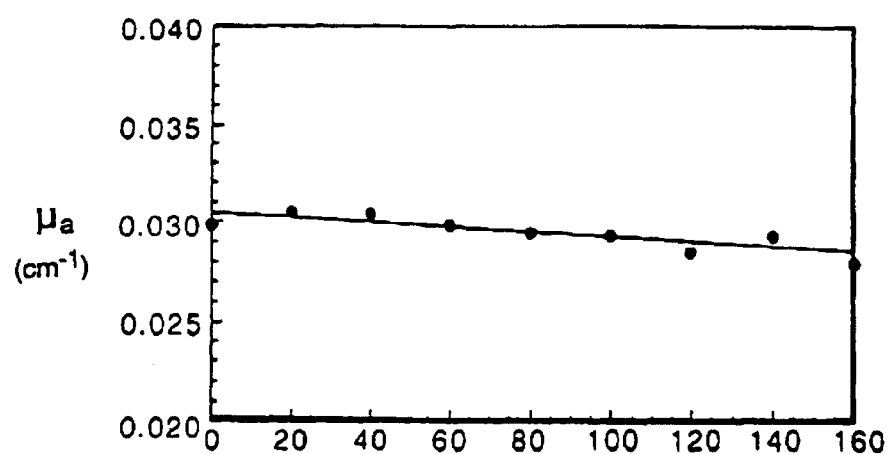

FIGS. 15(a)–(b) are plots of experimental results, measured with the continuous-wave method, of a 0.5% Intralipid-yeast-mannitol suspension.

Figure 16A:
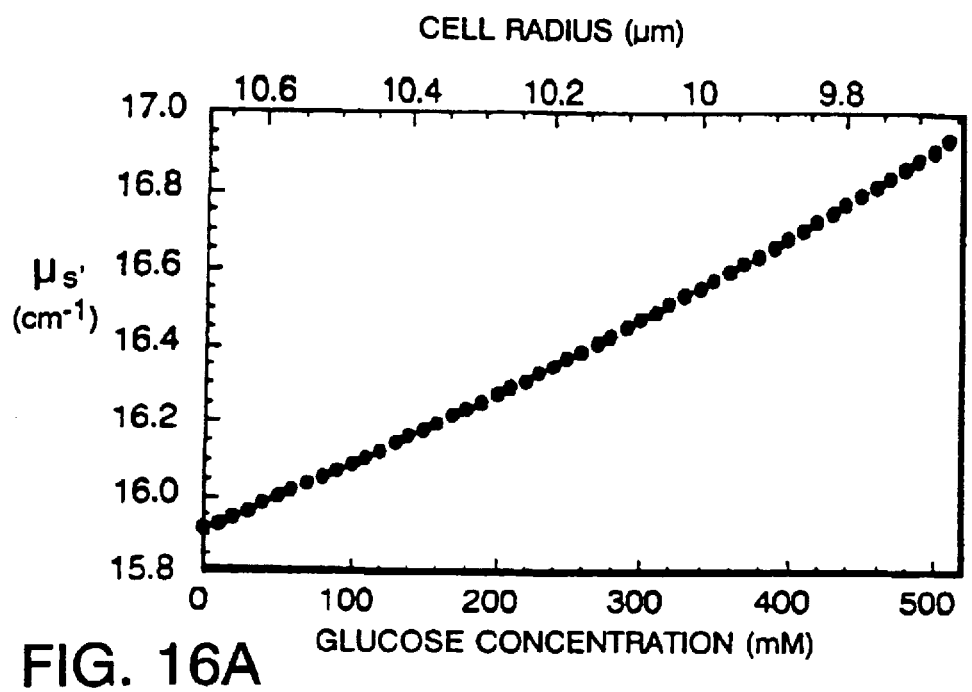
Figure 16B:
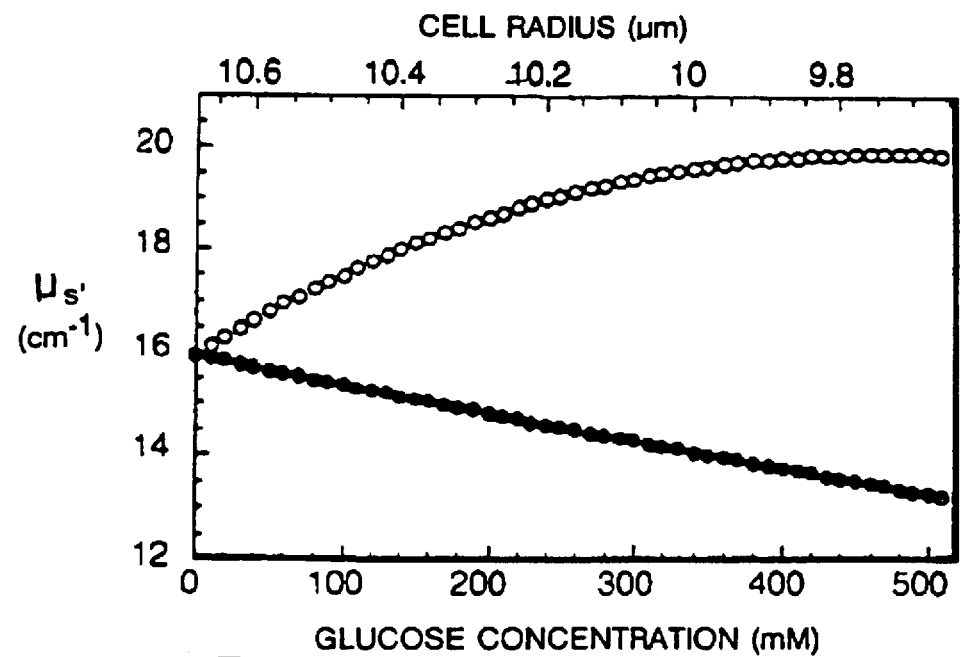

FIGS. 16(a)–(b) are a simulation of the reduced scattering coefficient $\mu_s'$, for a perfused liver, based on equation (12), with more realistic conditions.

FIG. 16(a) is a plot of the increase of $\mu_s'$ with a decrease in size of the liver cells (top scale) or with an increase in glucose concentration (bottom scale) in the perfusate.

FIG. 16(b) is a plot of the cell radius while the extracellular refractive index and the cell volume fraction are both fixed.

Figure 17A:
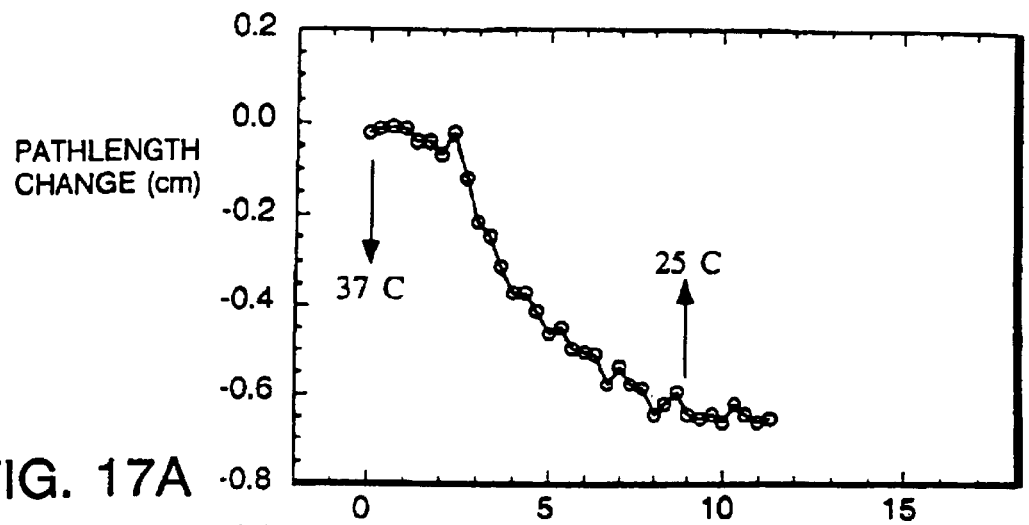
Figure 17B:
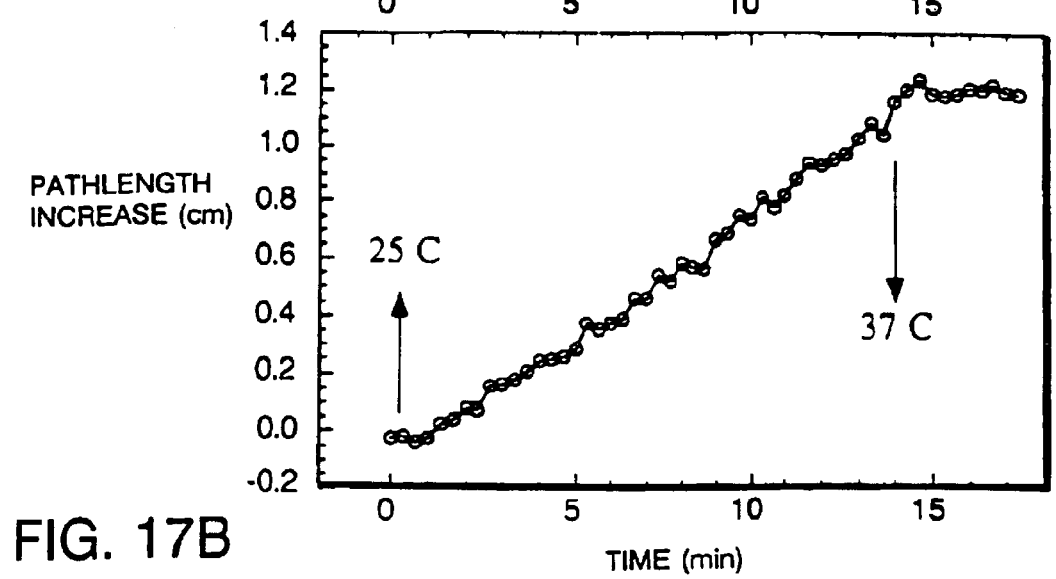

FIGS. 17(a)–(b) are plots showing the temperature-dependent pathlength change of a perfused rat liver for a cooling process (a) and warming-up process (b). The data were obtained by the frequency-domain method.

Figure 18A:
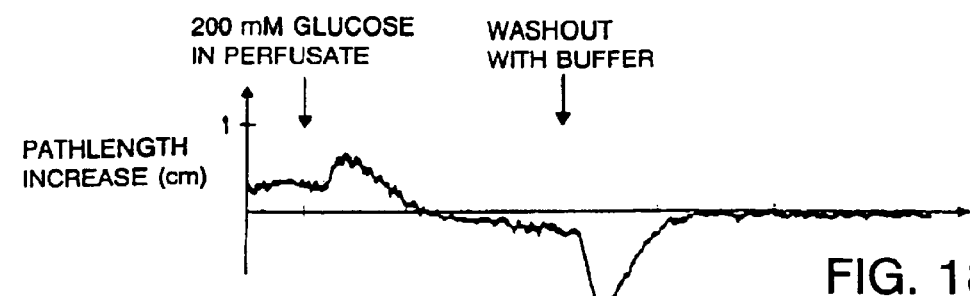
Figure 18B:
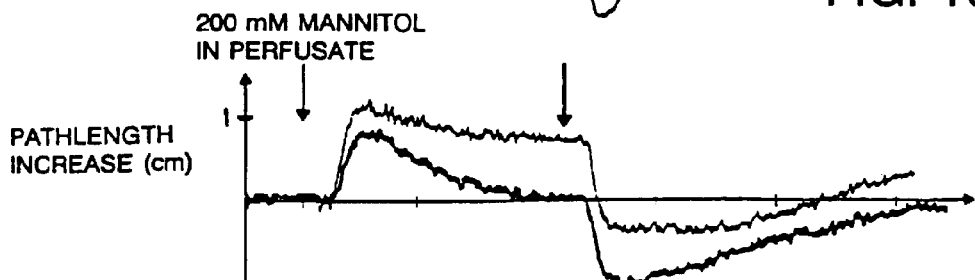
Figure 18C:
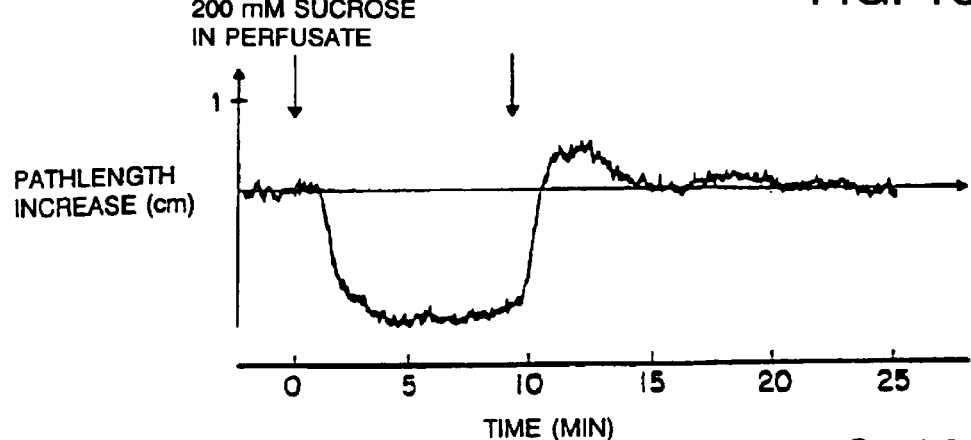

FIGS. 18(a)–(c) are plots of pathlength changes of a perfused rat liver with 200 mM glucose (a), 200 mM mannitol (b), and 200 mM sucrose (c), in the perfusate.

FIG. 19 is a plot of experimental results of the absorption coefficient $\mu_a$ (a), the reduced scattering coefficient $\mu_s'$ (b), and mean optical pathlength (c) of a rat liver perfused with 100 mM sucrose.

Figure 20:
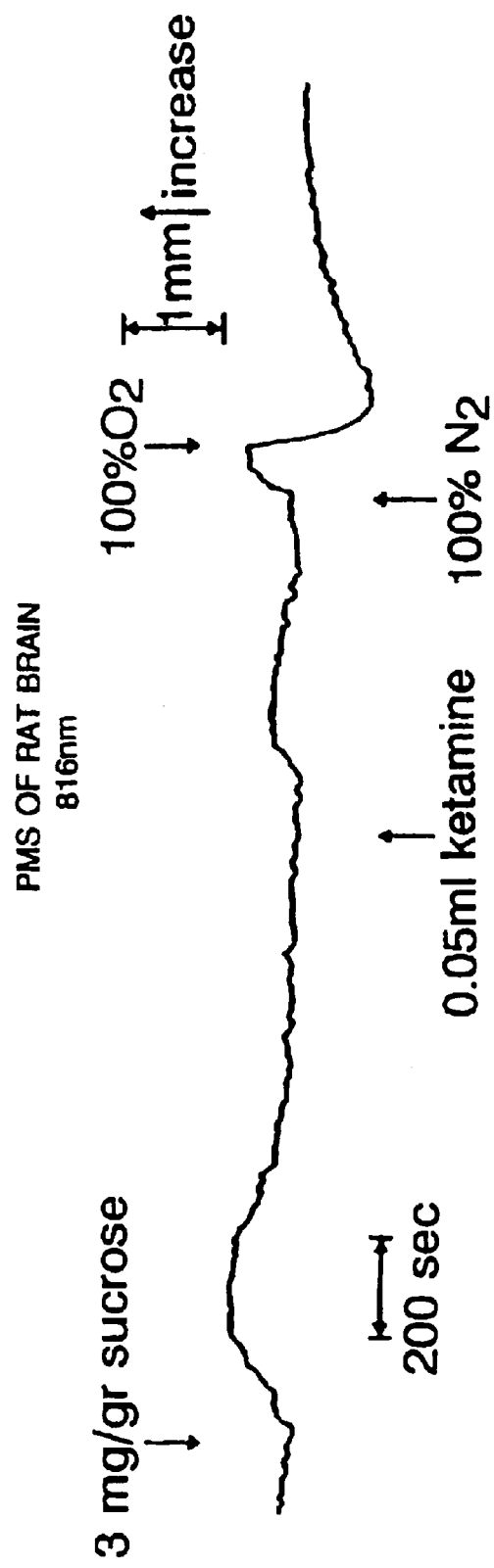

FIG. 20 is a PMS scattering change trace at 816 nm.

Figure 1A:
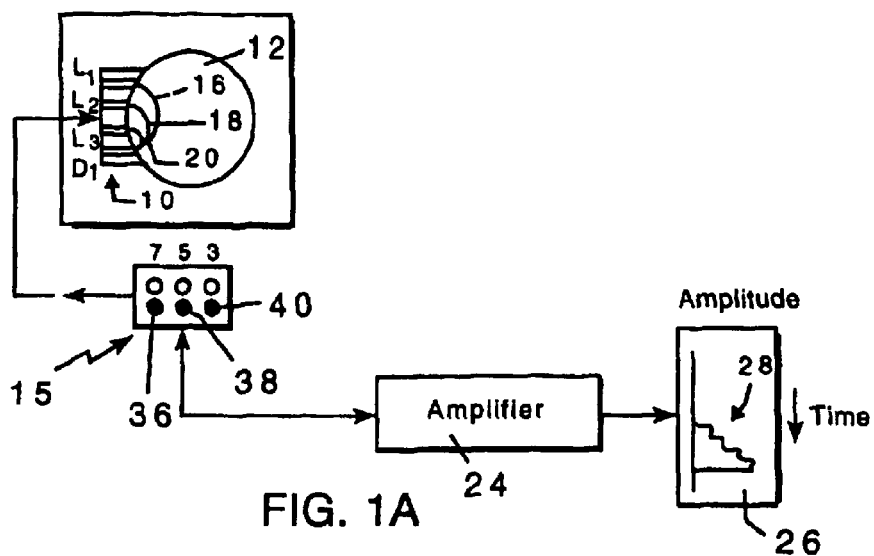
FIG. 1A is a diagrammatic sectional view of the monitor of FIG. 1 taken along the line 1A—1A.
Figure 1B:
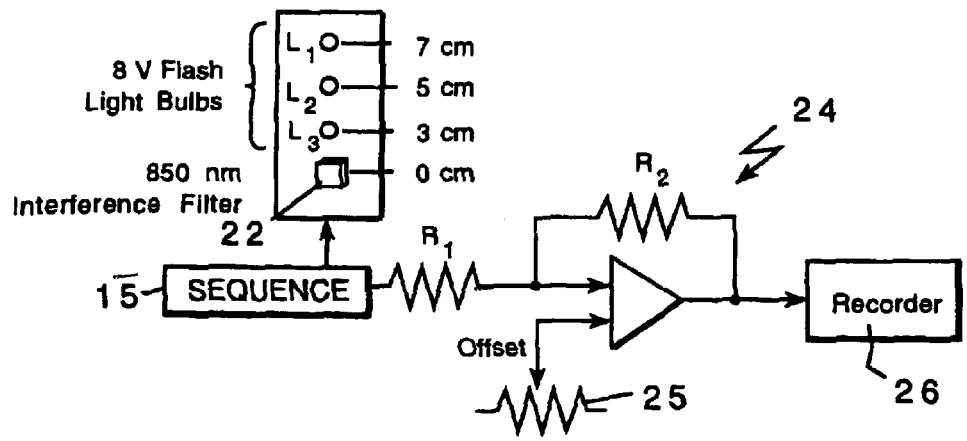
FIG. 1B is a diagrammatic side view of the monitor shown in FIG. 1A.
Figure 1:
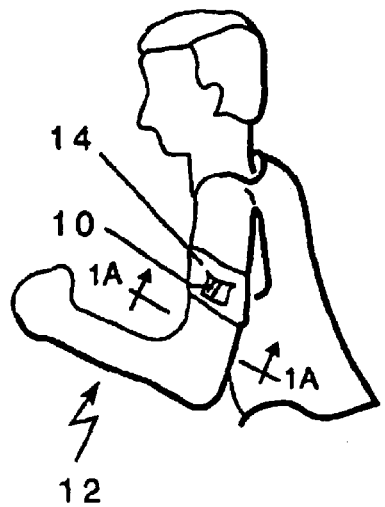
FIG. 1 is a diagrammatic side view of a monitor attached to the arm of a patient for monitoring the concentration of one or more solutes in the patient.

Referring to FIG. 1, a monitor 10 is attached to the surface of a biological system 12 (e.g., the arm of a patient) for non-invasively monitoring the concentration of one or more solutes (e.g., glucose) in the patient by using a novel optical technique. Monitor 10 is attached to the patient's arm by an adhesive bandage 14, although other means of attachment may be used (e.g., a stretchable arm wrap). Monitor 10 may be attached to other regions of the patient's body, e.g., head, breast, finger or belly, depending on the solute to be monitored and, e.g., the comfort level of the patient. Preferably the location of the monitor is selected to be where the extravascular solute level equilibrates with nearby blood vessels at a relatively rapid rate.

Monitor 10 uses a continuous light method and comprises a single detector DC amplifier system. This monitoring scheme has produced results that are compatible in sensitivity to those achievable by frequency-domain and time-domain methods. The signal-to-noise level of the changes observed with continuous light is ~0.01 milli OD at 850 nm with a 0.2 Hz bandwidth.

Referring to FIG. 1A, in a presently preferred embodiment, monitor 10 includes three spaced-apart light sources ($L_1$, $L_2$ and $L_3$; e.g., 8 volt flashbulbs) and a detector ($D_1$; e.g., a silicon photodiode). The light sources are respectively spaced different distances ($\rho_1$, $\rho_2$ and $\rho_3$, respectively) from the detector. For example, in the embodiment shown, $\rho_1$, $\rho_2$ and $\rho_3$ are equal to 7 cm, 5 cm and 3 cm, respectively.

The light sources deliver light into the patient's arm in sequence, which is controlled by a sequencer 15, and the delivered light migrates though a region of the patient's arm to the detector along one or more paths that can be respectively characterized by average path lengths 16, 18, 20. The distances between the light sources and the detector ($\rho_1$, $\rho_2$ and $\rho_3$) are respectively representative of these average path lengths. The lamp spacings from the detector may be varied, depending, e.g., on the size of the monitored region and on intrinsic noise levels. In certain preferred embodiments, the lamps should be spaced far enough apart to take advantage of the spacing effect and thus enhance the measurement accuracy. Although, in certain applications it is preferred that the lamps be spaced from the detector by at least 2 cm to achieve a simplification in the mathematics used to derive the solute concentration.

Figure 1C:
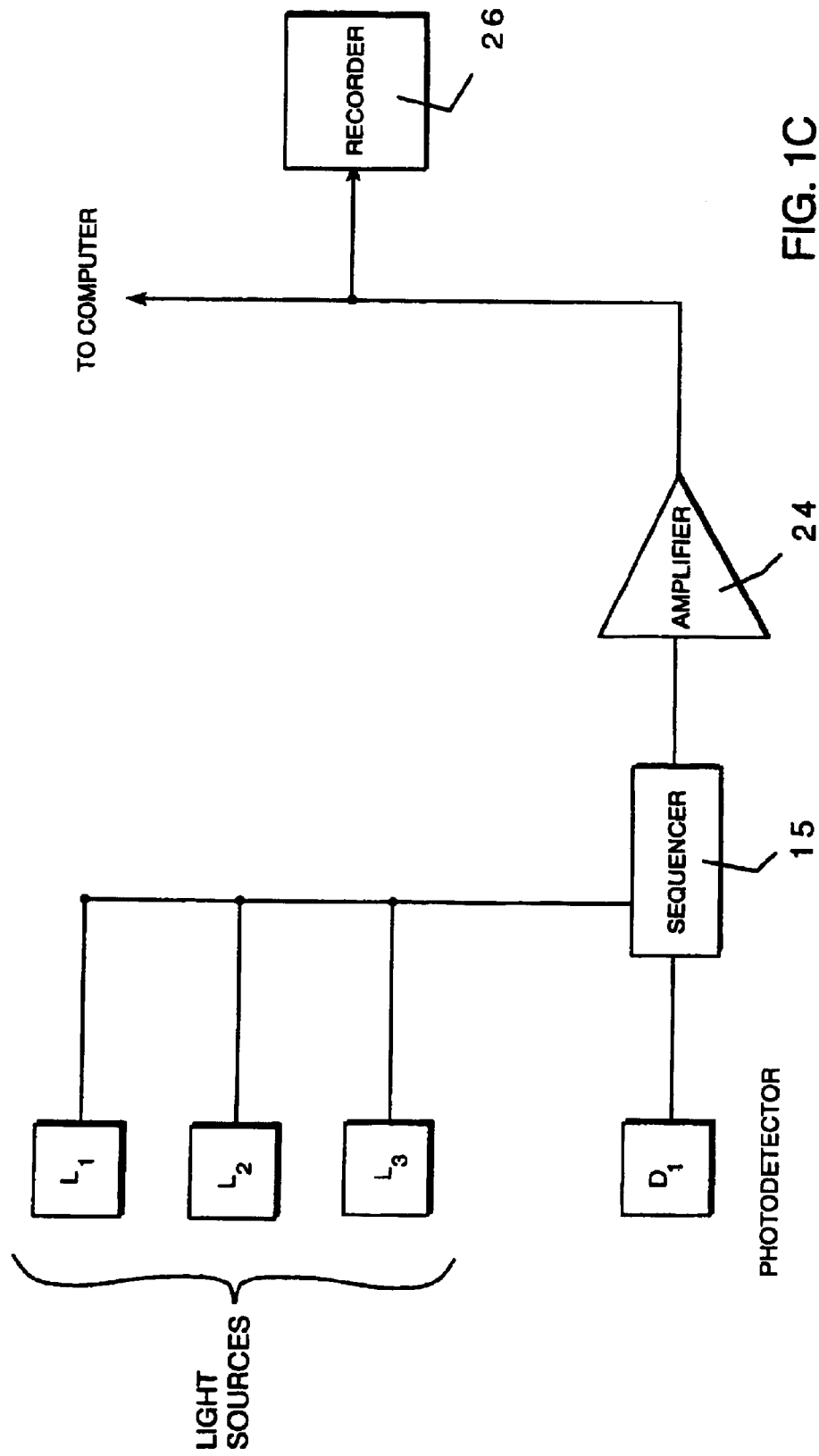
FIG. 1C is a block diagram of the monitor of FIG. 1.

As shown in FIGS. 1B and 1C, light received by detector $D_1$ first passes through an interference filter 22 having a passband corresponding to a wavelength of 850 nm. In the presently preferred embodiment, the interference filter is manufactured by Omega, Inc., and the silicon photodiode beneath it is Part No. F1227-66BR, available from Hamamatsu, having a large sensitive area for favorable signal to noise ratio and an NIR wavelength sensitivity. The sensitive area of the photodiode is approximately 6 mm². The silicon diode detector is connected to an amplifier 24 that is connected to a recorder 26 to give an intensity trace 28 as a function of time representative of the signals passing through a region of the patient's arm from the three light sources. Amplifier 24 drives the recorder with provision for offset of the zero point by adjustment of a potentiometer 25.

The three light sources are sequenced between the three sources at 20 sec. for each one. Light sequencer 15 contains three rheostats, which are adjusted to equalize the signals from the three lamps to give equal signal to noise ratios. The sequencer also contains three LED's 36, 38, 40 to indicate which lamp is sequenced. The sequencer applies not only the sequences to the three lamps but also flashes each light source on and off every half second so that a sample and hold circuit can monitor the difference between the light and dark signals. In this way, a stability of approximately $1 \times 10^{-5}$ optical density (OD) and a noise level of 0.1 of this is obtained with a response time of 1–2 seconds. In one embodiment, sequencer 15 is an independent source for determining the frequency of lamp flashing. Lamps flash at frequency of ½ Hz or 2 flashes per second or greater. In operation, one lamp flashes, the signal is picked up by the photodetector and while the lamp is on the intensity is measured and stored on the chart recorder or in computer memory.

All the data is acquired and compared with a chart recorder 26, and the zero value established with the light-off condition. The output of amplifier 24 may alternatively be sent to an electronic display unit (e.g., an LCD display). The analog signal from amplifier 24 may be digitized in the display unit and displayed as a digital number. The signal is also sent to a comparator (e.g., a computer) for comparing the measured light intensities from different source-detector positions against a predetermined calibration scale to provide a measure of solute concentration.

The three rheostats are adjusted to ensure that the signal intensities detected from the three light sources are equal during a calibration mode, described below. Thus, abscissa of the plots shown herein correspond to the base line obtained for the scatterer only condition (i.e., equal signals from all 3 light sources). The signal obtained during the calibration mode is termed $I_0$. The recorder gain may be increased to a desired level to obtain a desired sensitivity level, e.g., by factors of 2, 5, or 10. The measured signals are multiplied by this factor (i.e., 200, 500, 1000). Deflections of the three signals caused by changes in solute concentration are calculated as a percentage of the initial value ($I_0$) and multiplied by 0.00434 to convert to $\log_{10}$ for absorbency changes of less than 10% (ΔOD). Otherwise, $\log_{10}$ is computed.

Figure 1D:
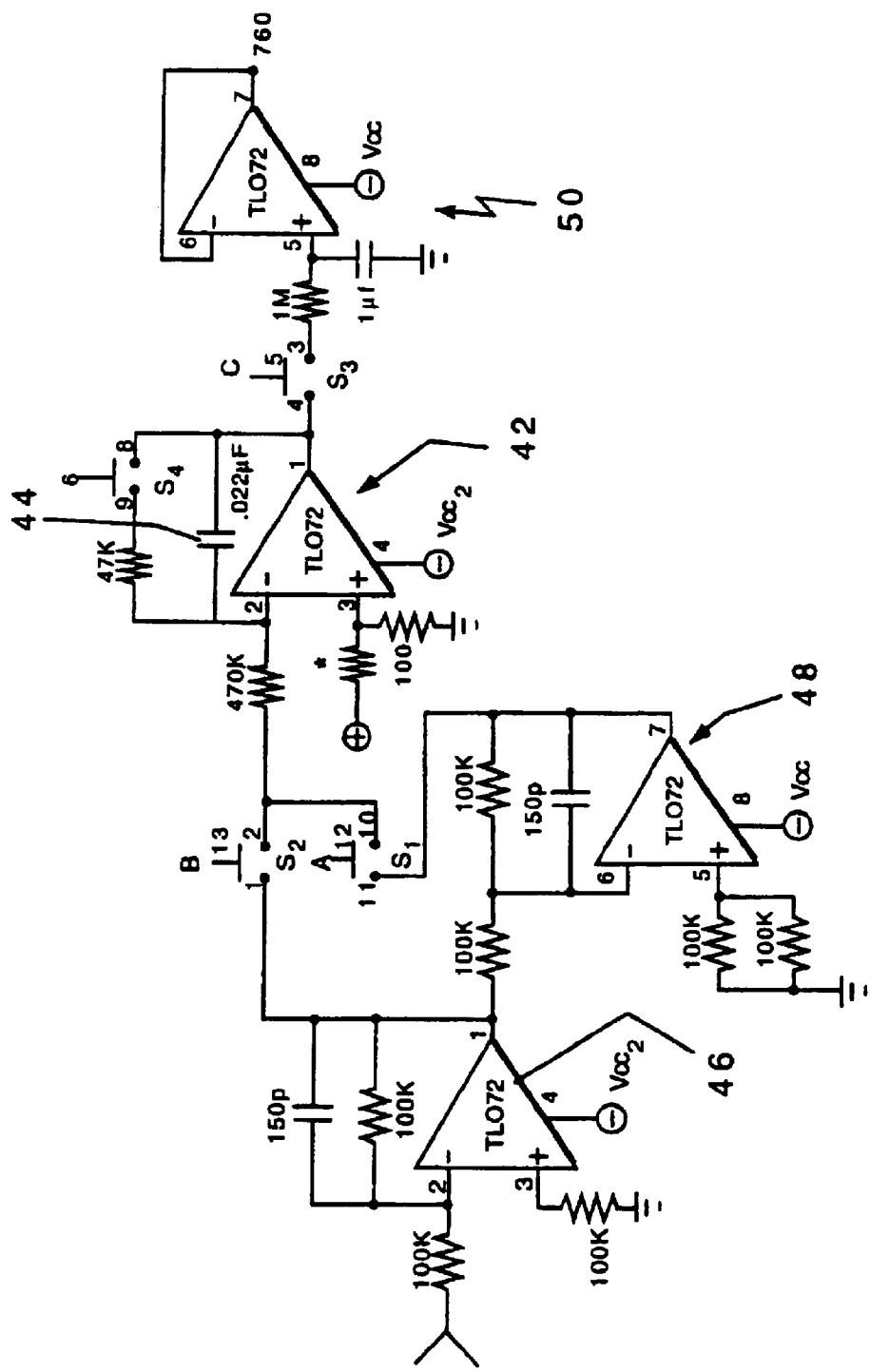
FIG. 1D is a schematic diagram of a circuit corresponding to a section of a sequencer.

Referring to FIG. 1D, sequencer 15 enables correction for the dark current/noise that comprises background light, DC offset of the operational amplifiers, photodiode dark current, temperature effects on the outputs of individual components and variations due to changing environment. The dark current/noise correction is explained in connection with a circuit 40. Monitor 10 performs data acquisition in four steps which are synchronized by the sequencer. In the first step, the lamps are off. The output of the detector is directed to an integrator 42 and an integration capacitor 44 is charged to the dark level voltage. In the second step, one of the lamps is turned on. The preamplifier output that corresponds to the intensity of the detected light is directed to integrator 42 in a way to charge capacitor 44 with current of polarity opposite to the polarity of the charging current in the first step. This is achieved using appropriate ON/OFF combination of switches S1 and S2. The voltage of capacitor 44 is charging to a value which, at the end of this step, represents the total signal minus the dark level noise signal. In the third step, both switches S1 and S2 are turned OFF to disconnect both the positive unity gain and the negative unity gain operational amplifiers (46 and 48). Then, the output of integrator 42 is moved via switch S3 to a hold circuit 50 which also functions as a low pass filter. This output is the detected signal corrected for the background noise. In the fourth step, the switches S1, S2 and S3 are open and switch S4 is closed in order to discharge capacitor 156 through a 47K resistor. At this point, the circuit of integrator 154 is reset to zero and ready for the first step to be applied to the next lamp in the sequence.

In an alternative embodiment, the RUNMAN™ system described in International Publication No. WO 92/20273, filed May 18, 1992, which is herein incorporated by reference, may be used to detect the lamp signals migrating through the biological system. In this embodiment, the RUNMAN™ system is configured as described above and modified for single wavelength measurement (e.g., 850 nm).

Figures 2A, 2B:
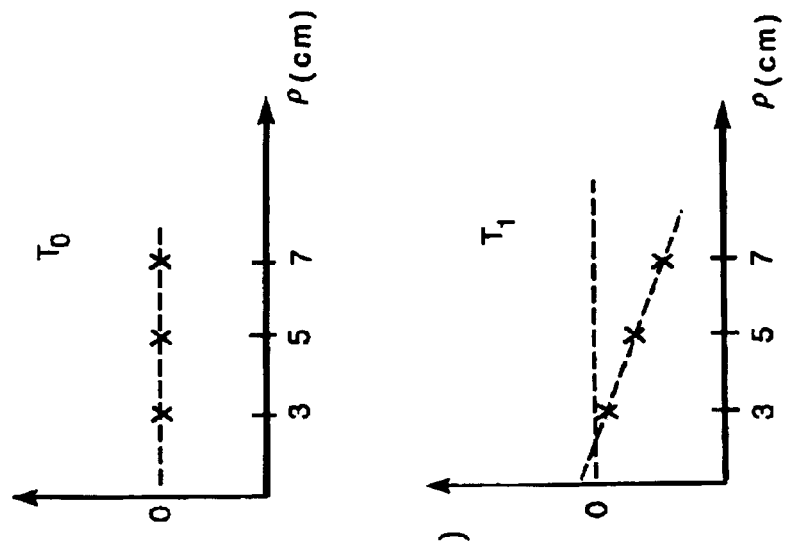
FIGS. 2A and 2B are plots of optical density (OD) as a function of detector-light source separation (ρ) corresponding to the time periods ($T_0$, $T_1$) of FIG. 2.
Figure 2:
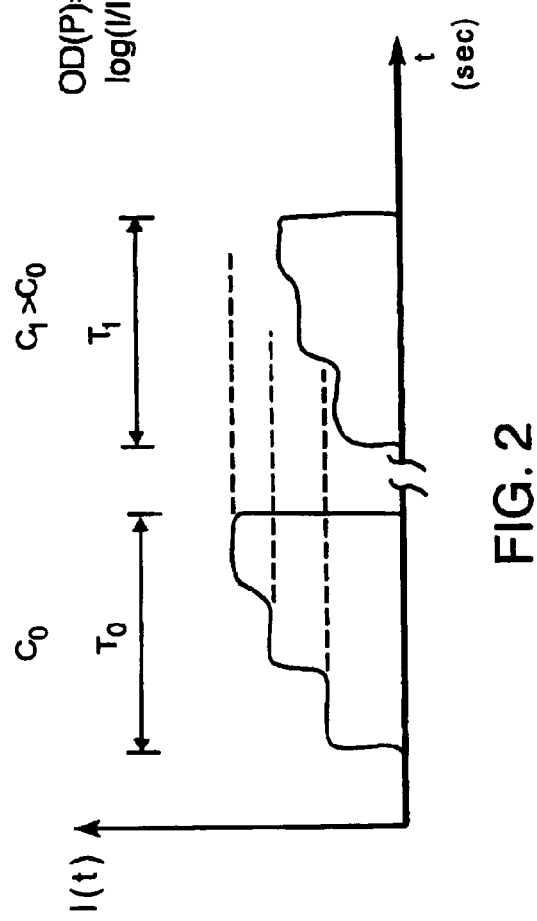
FIG. 2 is a plot of intensity as a function of time at two different time periods ($T_0$, $T_1$) during which the solute concentration level increased from $C_0$ to $C_1$.

As shown in FIGS. 2–2B, the measured results are plotted as optical density (OD) as a function of light source separation ($\rho_1$, $\rho_2$ and $\rho_3$). The OD is defined as $$OD = \log\left(\frac{I_0}{I}\right) \quad (1)$$

where, $I_0$ is the calibrated initial intensity and I is the detected intensity, which varies over time in this example as shown in FIG. 2. The plots of OD versus $\rho$ are linear for values of intralipid up to 1% (as discussed in detail below) and may show a non-linearity above that value for the largest detector light-source separation. In such a case, the smaller separations are used.

The best straight line or computer fit (e.g., by minimizing least mean square error) to the three data points for each measurement period ($T_0$, $T_1$) gives the slope in OD per solute concentration (usually 1 millimolar), and the extrapolation of the line to the ordinate gives the intercept. In some cases, a two-point slope is calculated (e.g., when only two sources are used, or when a data point corresponding to the largest source-detector spacing is subject to severe nonlinearity).

Similar plots of the variation of slope and intercept with solute and scatterer concentration are made, from which the final measures, namely OD per millimole solute per percent intralipid or per degree C. are computed (as described in detail below). This gives the sensitivity parameter employed in this study.

Theory

According to diffusion theory, the intensity of continuous light remitted through a semi-infinite scattering medium, such as tissue, depends on the tissue absorption and scattering properties ($\mu_a$ and $\mu_s'$). The detected signal I($\rho$), at a separation of $\rho$ from the source can be given as $$r_1 = \sqrt{\left(\frac{1}{\mu_t'}\right)^2 + \rho^2}, \; r_2 = \sqrt{\left(\frac{\frac{4}{3}+1}{\mu_t'}\right)^2 + \rho^2}, \quad (2)$$

$$\mu_t' = \mu_a + \mu_s', \; \mu_{eff} = \sqrt{3\mu_a(\mu_a+\mu_s')}.$$

and A is a parameter dependent upon the refractive index of the tissue and the initial light source intensity. When the source detector separation is larger than 2 cm, this equation can be simplified as $$I(\rho) = \frac{1}{a\mu_t'}\left(\mu_{eff}+\frac{1}{\rho}\right)\frac{e^{-\mu_{eff}\rho}}{\rho^2} \quad (3)$$

$$\ln[\rho^2 I(\rho)] = -\mu_{eff}\rho - \ln[a\mu_t] + \ln\left[\mu_{eff}+\frac{1}{\rho}\right] \quad (4)$$

By having a calibration model with known values of $\mu_a$ hd a(cal) and $\mu_s'$ (cal), we can compare an unknown sample to it, based on $$\ln[\rho^2 I_0(\rho)] - \ln[\rho^2 I(\rho)] = \quad (5)$$

$$\rho[\mu_{eff} - \mu_{eff}(\text{cal})] + \ln\left[\frac{\mu_t}{\mu_t(\text{cal})}\right] + \ln\left[\frac{\mu_{eff}(\text{cal})+1/\rho}{\mu_{eff}+1/\rho}\right]$$

If the unknown and calibration samples have a small difference in optical properties, the last term of Eq. (5) can be negligible. Therefore, we can define the optical density such that $$OD = \log\left(\frac{I_0}{I}\right) = m\cdot\rho + b \quad (6)$$

where m is the slope and b is the intercept of the OD versus $\rho$ line, given by:

$$m = \sqrt{3}\left(\sqrt{\mu_a\mu_s'} - \sqrt{\mu_a(\text{cal})\mu_s'(\text{cal})}\right) \quad (7)$$

$$b = \log\left(\frac{\mu_a+\mu_s'}{\mu_a(\text{cal})+\mu_s'(\text{cal})}\right)$$

where $\mu_a$ (cal) and $\mu_s'$ (cal) are the absorption and reduced scattering coefficients of the calibrated sample and $\mu_a$ and $\mu_s'$ are the absorption and reduced scattering coefficients of the sample to be monitored. By measuring OD versus the source detector separation, we can obtain slope (m) and intercept values (b). With the measured values of slope and intercept, we can obtain values for $\mu_a$ and $\mu_s'$ by solving Eq. 7 as follows.

$$\mu_a = \frac{1}{2}\cdot\left(y - \sqrt{y^2-4x}\right) \quad (8)$$

$$\mu_s' = \frac{1}{2}\cdot\left(y + \sqrt{y^2-4x}\right)$$

where, $$x = \mu_a\mu_s' = \left[\frac{m}{\sqrt{3}} + \sqrt{\mu_a(cal)+\mu_s'(cal)}\right]^2 \quad (9)$$

$$y = \mu_a + \mu_s' = [\mu_a(cal)+\mu_s'(cal)]10^b$$

Eq. (6) exhibits a linear relationship between OD and the source-detector separation ($\rho$). The slope and intercept of this equation are studied here by measuring OD versus $\rho$.

Figure 3:
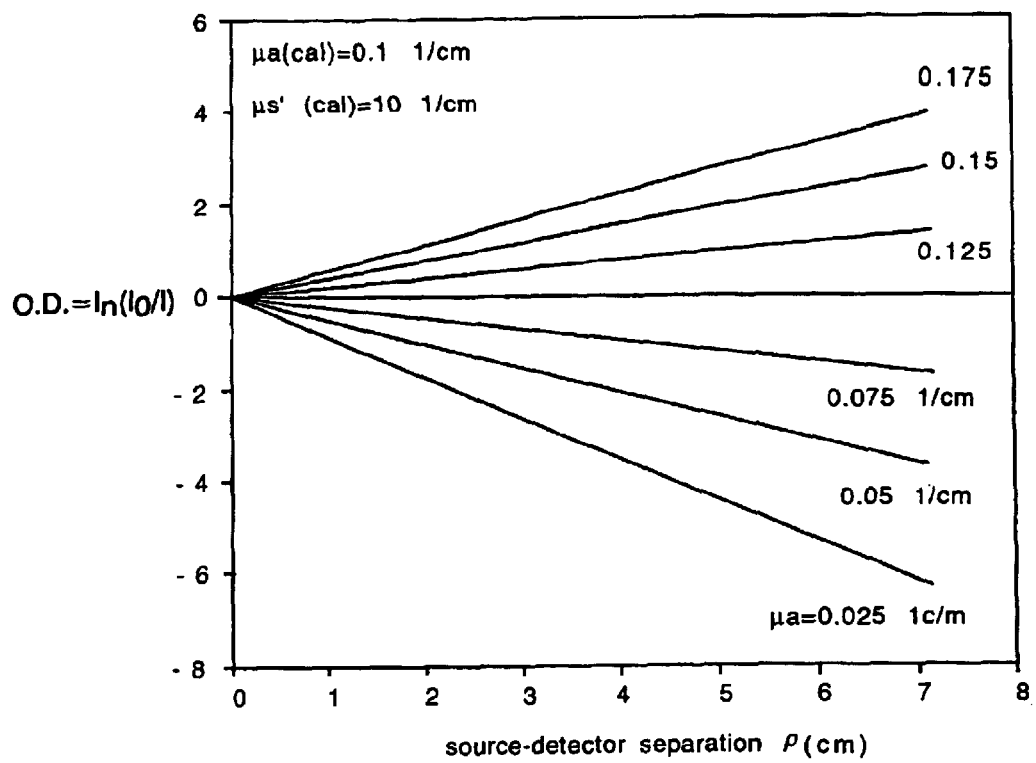
FIG. 3 is a plot of a calculated variation of the absorption coefficient ($\mu_a$) as a function of source-detector separation (ρ).

FIG. 3 shows a calculated result of OD versus source-detector separation as a function of absorption change of the measured sample. The calibration sample used here has $\mu_a$ (cal) and $\mu_s'$ (cal) values of 0.1 cm$^{-1}$ and 10 cm$^{-1}$, respectively, indicated by the standard horizontal line in the figure.

Figure 3A:
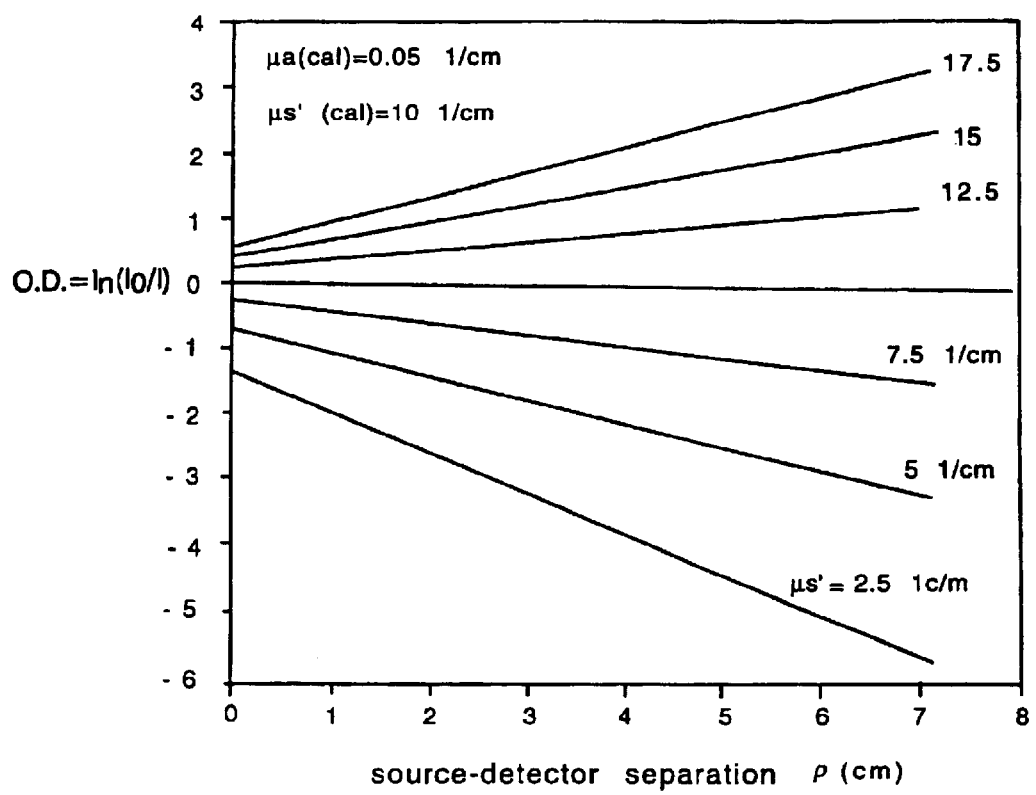
FIG. 3A is a plot of a calculated variation of the absorption coefficient ($\mu_s'$) as a function of source-detector separation (ρ).

FIG. 3A gives the slope and intercept dependence on the scattering property of the measured sample for the same calibrations. Above $\mu_s'$, =10 cm$^{-1}$, the slope and intercept are of equal sensitivity, while the intercept is more sensitive below $\mu_s'$, =10 cm$^{-1}$. FIG. 3A shows that the slope and intercept are negative if $\mu_s$ (sample)<$\mu_s'$ (cal), and the slope and intercept are positive if either $\mu_s$ (sample>$\mu_a$ (cal). Therefore, by determining the slope and intercept of OD versus source-detector separation, one can characterize the absorption and scattering properties or changes of an unknown sample with respect to the calibration sample, i.e., a relative $\mu_a \mu'_s$ is determined, as contrasted to frequency-domain or time-domain studies.

Figure 4:
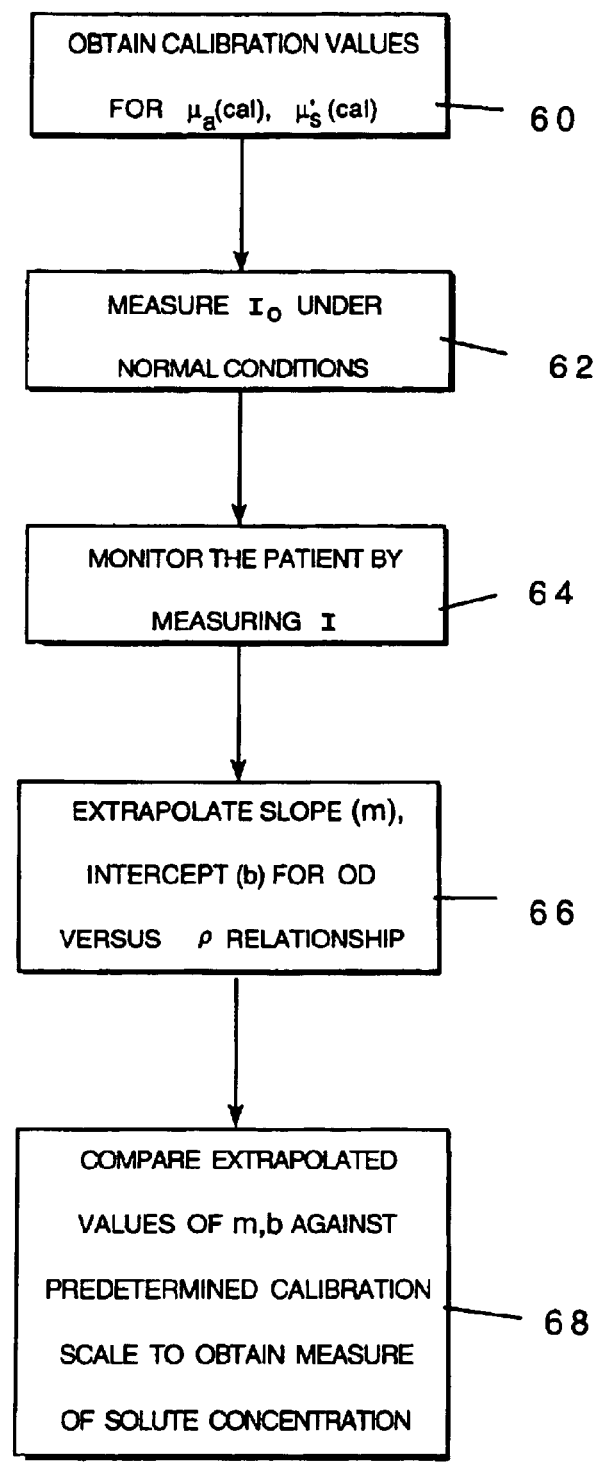
FIG. 4 is a flow diagram of a method for monitoring solute concentration.

Referring to FIG. 4, the concentration of one or more solutes in a biological system, e.g., a patient, may be monitored by the following process. Obtain calibration values $\mu_a$ (cal) and $\mu_s'$ (cal) corresponding to the intrinsic absorption and reduced scattering coefficients for a patient (step 60). These calibration values may be obtained using well known optical techniques (e.g., TRS or PMS) and need only be determined once for a given patient. These calibration values vary from patient to patient due to variations in skin pigmentation, variations in thicknesses of different skin layers, etc. Measure the so-called initial intensity $I_0$ for the patient under conditions that will be considered reference conditions (e.g., when the patient's biological systems are operating normally) (step 62). This initial intensity is used as the reference intensity for determining the determined optical density (OD; Eq. 1). Monitor the concentrations of one or more solutes in the patient by measuring the intensity (I) detected by the system described above for at least two different source-detector spacings ($\rho$) (step 64). The intensity (I) can then be used to determine a best linear fit to the at least two (OD, $\rho$) data points. Extrapolate slope (m) and intercept (b) values from the measured (OD, $\rho$) data points (step 66). Compare the extrapolated slope (m) and intercept (b) values against a predetermined calibration scale (e.g., as described below) to obtain a measure of solute concentration (step 68).

This monitoring process is preferably implemented in hardware (e.g., an ASIC) or as a software program run on a computer or other processor.

Calibration Scale

A calibration scale for relating the slope and intercept data monitored using the above-described technique to obtain a measure of one or more solute concentrations can be derived from measurements of a simulated biological environment or actual biological tissue.

According to a recent study by Graaff et al., (R. Graaff, et al., Appl. Opt. 31(10), 1370–1376 1992), the Mie theory can be well approximated to give the following expression for the reduced scattering cross section, $\delta_s'$, $$\sigma'_s = \sigma_s(1-g) = 3.28\pi a^2 \left(\frac{2\pi a}{\lambda}\right)^{0.37}\left(\frac{n_{in}}{n_{ex}} - 1\right)^{2.09} \quad (10)$$

where $\delta_s$ is the scattering cross section, g is the average cosine of the scattering angle, a is the radius of the scattering particle, $\lambda$ is the wavelength of the scattered light, $n_{in}$ and $n_{ax}$ are refractive indexes of the intracellular and extracellular fluid, respectively. In the case of model or cell suspension systems, $n_{in}$ and $n_{ax}$ represent refractive indexes of the scattering particle and suspension solution, respectively. Three restrictions for validation of equation (10) are a) g factor has to be larger than 0.9 (g>0.9); b) the particle radius and wavelength of scattered light satisfies 5<(2$\pi$a/$\lambda$)<50;c) the refractive index relative to the surrounding medium is limited in the range of 1<$n_{in}/n_{ax}$<1.1. With the use of near-infrared light, these three conditions are satisfied for scattering in living tissues and blood, (R. Graaff, et al., 1992).

In a highly multiple-scattering medium, the reduced scattering coefficient, $\mu_s'$, is related to $\delta_s'$ by $\mu_s' = \lambda \delta_s'$, where $\lambda$ is the total number of the scattering particles per unit volume, (A. Ishimaru, Wave Propagation and Scattering in Random Media, Academic Press, Inc. San Diego, 1978). This number density, $\lambda$, can be given as $\phi/v_{par}$, where $\phi$ is the volume fraction of the particles relative to the total volume, and $v_{par}$ is the volume of a single scattering particle, (B. Beauvoit et al., Biophys. J. 67, 2501–2510 1994), and can be expressed $$\frac{4}{3}\pi a^3$$

for a spherical scatterer. Substituting $\delta_s'$ by equation (10), we have $$\mu'_s = \frac{\phi}{v_{par}}\sigma'_s = \frac{2.46}{a}\phi\left(\frac{2\pi a}{\lambda}\right)^{0.37}\left(\frac{n_{in}}{n_{ex}} - 1\right)^{2.90} \quad (11)$$

Figure 12A:
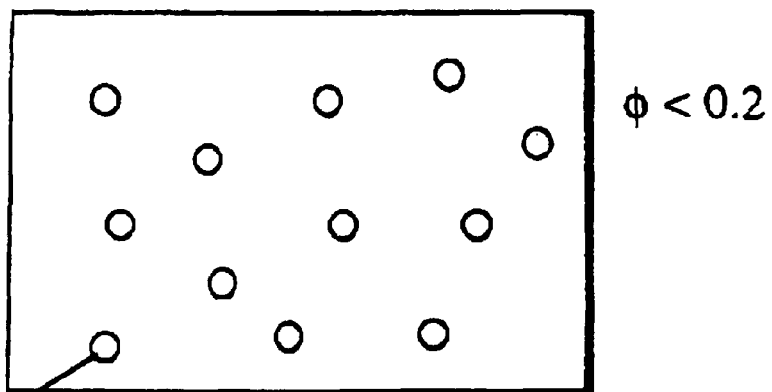
FIG. 12 is a schematic diagram illustrating the difference in volume fraction of scattering particles between a scatterer suspension (a) and tissue or blood (b).
Figure 12B:
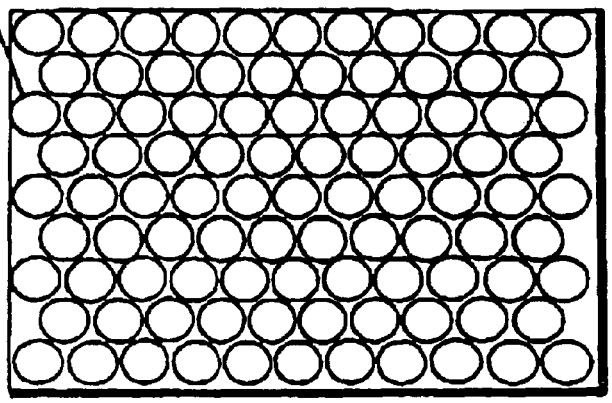

This equation is valid for sufficiently small $\phi$ ($\phi$<0.2), such as in cell or scatterer suspensions. For $\phi$<0.5, which is very common for scatterers in tissue and blood, the scattering particles are densely packed, and the whole solution may be viewed as a homogeneous medium with the scattering particles made of the inter-particle space. These two cases are schematically illustrated in FIGS. 12(a) and 12(b), respectively. In the limit of $\phi$–<1, the inter-particle space disappears and $\mu_s'$ should approach 0. Based on this consideration, we employ the strategy developed by Ishimaru (A. Ishimaru, 1978) and others (L. Reynolds et al., Appl. Opt. 15, 2059–2067, 1967), (J. M. Steinke et al., Appl. Opt. 27, 4027–4033, 1988) for red blood cells and give the following modified expression of $\mu_s'$ for biological tissues:

$$\mu'_s = \frac{\phi(1-\phi)}{v_{par}}\sigma'_s = \frac{2.46}{a}\phi(1-\phi)\left(\frac{2\pi a}{\lambda}\right)^{0.37}\left(\frac{n_{in}}{n_{ex}} - 1\right)^{2.09} \quad (12)$$

Both equations (11) and (12) show that $\mu_s'$ has both a refractive-index-dependent factor, $$\left(\frac{n_{in}}{n_{ex}} - 1\right)^{2.09}$$

and a size-dependent factor, either $$\frac{\phi}{a}\left(\frac{2\pi a}{\lambda}\right)^{0.37}$$

for suspensions or $$\frac{\phi(1-\phi)}{a}\left(\frac{2\pi a}{\lambda}\right)^{0.37}$$

for tissue.

The diffusion approximation of transport theory has been widely used as the theoretical basis to describe light propagation within a highly scattering medium for a given geometry [18] (E. M. Sevick et al., Anal. Biochem. 195, 330–351, 1991) and [19] (S. R. Arridge et al., Phys. Med. Biol. 37, 1531–1560, 1992). The solution of the time-domain diffusion equation allows to calculate the mean optical pathlength, <L>, of light traveled before detection by <L>= c<t>, where c is the speed of light traveled in a mean time, <t>, in the scattering medium. In a semi-infinite, reflectance geometry, <t> can be given as $$\langle t \rangle = \frac{\int R(\rho, t) t \, dt}{\int R(\rho, t) dt'} \quad (13)$$

where $R(\rho,t)$ is the reflectance of impulse light detected on the medium surface at time, t, and at distance, ρ, away from the light source. After substituting $(ρ t)$ in <t> and simplifying <t>, we obtain an expression relating the mean optical pathlength, <L>, to the absorption ($\mu_a$) and reduced scattering ($\mu_s'$) coefficients by $$\langle L \rangle = \frac{\sqrt{3}}{2} \rho \sqrt{\frac{\mu_s'}{\mu_a}} \left[ \frac{1}{1 + \frac{1}{\rho \sqrt{3 \mu_a \mu_s'}}} \right]. \quad (14)$$

So <L> can be a marker to monitor a change in absorption or scattering properties in the medium under study. Furthermore, the first order approximation of eq. (5) is $$\langle L \rangle = \frac{\sqrt{3}}{2} \rho \sqrt{\frac{\mu_s'}{\mu_a}} - \frac{1}{2\mu_a} \quad (15)$$

indicating that an increase in scattering results in an increase in optical pathlength.

Volume Regulatory of Cells and Effect of Solution Composition on Nonelectrolyte-Induced Shrinkage Depending on the species and the tissue type, the volume change of cells upon exposure to anisosmotic media is subjected to a regulation. For instance, if hepatocytes (liver calls) are suddenly exposed to a hypotonic medium, they initially swell, but within minutes they can regain almost their original volumes. This behavior has been named Regulatory Cell Volume Decrease and is governed by the activation of $K^+$ and Cl Efflux. On the other hand, if the cells are suddenly exposed to a hypertonic medium, they initially shrink, but within minutes they attain almost their initial volumes. This behavior has been named Regulatory Cell Volume Increase and is caused by the activation of $na^+$ and Cl influx. However, neither the Regulatory Volume Increase nor Decrease completely restore the initial cell volume, and the liver cells are left in either a slightly swollen or shrunken state. In addition, the mechanisms of the regulation of the cellular volume at the cellular (nature of ions) and at the molecular level (carriers responsible for ions efflux or influx) are different from one tissue type to another one, (D. Haussinger et al, Biochim. Biophys. Acta 1071, 331–350, 1991).

In the liver, when hepatocytes are subjected to hypertonic stress by the addition of a carbohydrate into the extracellular medium, there is either no or only a partial recovery from the shrunken state depending on the nature of the carbohydrate. For instance, the time-course of the sorbitol-induced shrinkage does not show any Regulatory Volume increase, (T. Bakker-Grunwald, Biochim. Biophys. Acta 731, 239–242 1983). In contrast, sucrose and mannitol-induced shrinkage is followed by a partial recovery of the initial volume. These discrepancies have been explained by different permeability of the hepatocyte toward the three nonelectrolytes used in the studies. The higher is the cellular permeability to the sugar, the faster is the equilibration of the osmolarity between the two compartments, and the faster is the recovery from the shrunken state (P. Haddad, et al, Am. J. Physiol. 256, G563–G569 1989), (G. Alpini et al, Am. J. Physiol. 251, C872–C882, 1986).

EXAMPLE 1

Figure 5A:
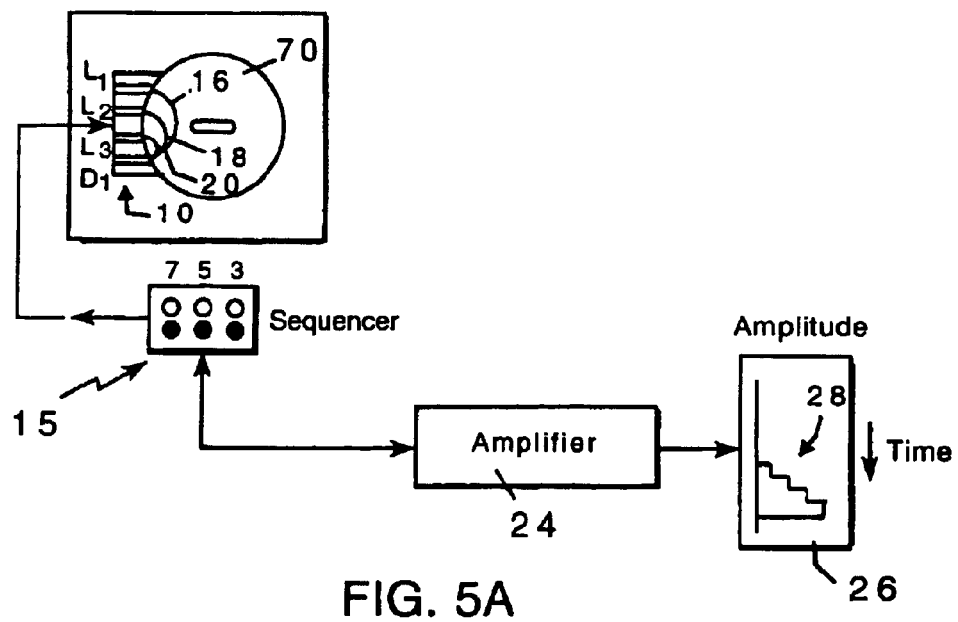
FIGS. 5 and 5A are diagrammatic side views of a calibration model and a monitor used for obtaining a calibration scale, respectively.
Figure 5:
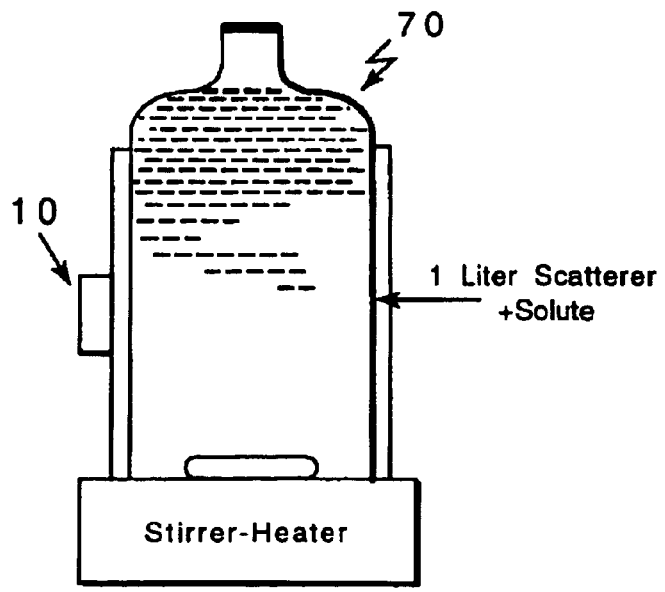

The layout of the components is illustrated in FIGS. 5 and 5A, which shows the tissue model as a 10 cm diameter cylinder 70 filled with one liter of a scatterer (e.g., intralipid). The slopes and intercepts are computed per 1% scatterer per millimolar (mM) solute per cm input/output at 25° (see FIG. 6).

In order to simulate the detection of solute in a breast, brain, or other portion of the human body, we have employed a cylindrical vessel of 10 cm in diameter and 10 cm in height, to which the optical detector is attached. The vessel is filled with distilled water to which appropriate concentrations of scatterer, for example, intralipid (0.1–2% by volume) are added. The vessel filled with a scattering medium with no solute present may be used as the calibration standard for $\mu_a$ and $\mu_s'$. The solute is then added in increasing concentrations as solid or liquid and dissolved or mixed appropriately by the rapid motion of the stirrer bar. Dilution of the scatterer is measured by dilatometry. Thus, relationships between absorbency changes due to the solute and scatterer concentrations are obtained.

Figure 7:
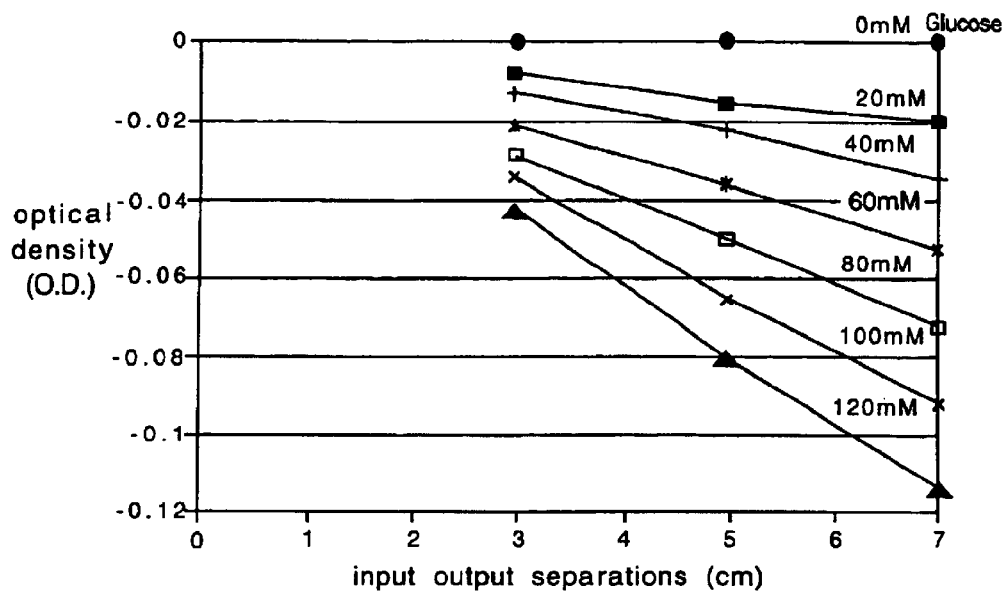
FIG. 7 is a plot of optical density (OD) as a function of input-output separation (ρ).

FIG. 7 illustrates the results of a typical experiment in 1% intralipid as a scatterer with solute additions of 10, 50, 100, etc. grams of glucose to 1 liter of 1% intralipid. OD decreases as a function of ρ, for 20 mM increments of glucose; both the slope and the intercept are affected. The errors due to instrument noise are approximately $1 \times 10^{-5}$ OD as compared with the 120 milli-OD scale of the data shown here. In this case an approximately linear relationship of OD and ρ are obtained according to Eqs. 6 and 7.

Figure 7A:
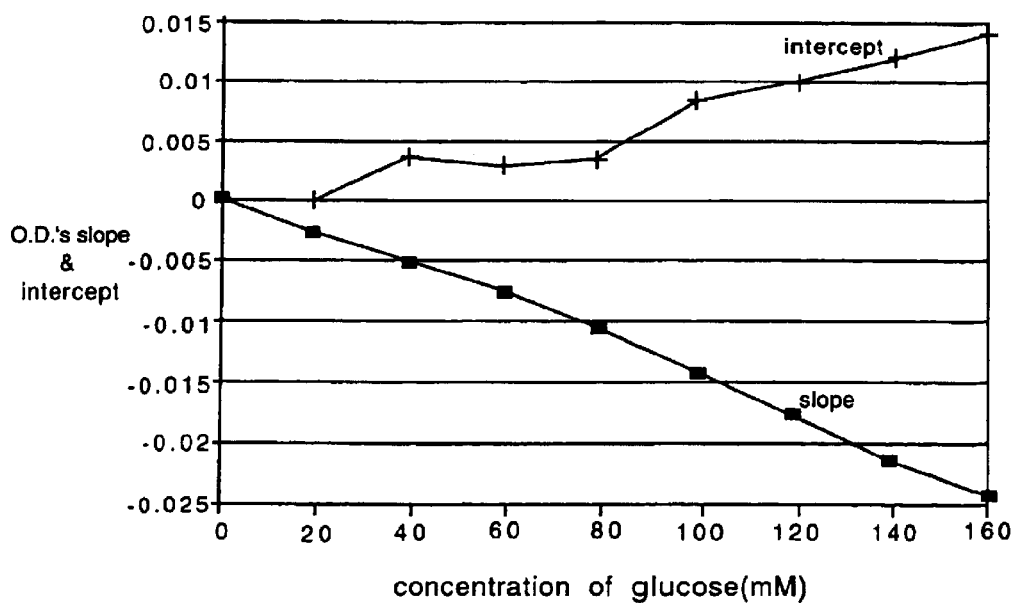
FIG. 7A is a plot of the slope and intercept extrapolated from the plot of FIG. 7 as a function of glucose concentration.

The relation between solute concentration, slope, and intercept (replotted from FIG. 7) is given in FIG. 7A, and the values are given in Table 1; slope and intercept values show $1.5 \times 10^{-4}$ OD and $0.91 \times 10^{-4}$ OD per mM of glucose and a 1 cm separation of input/output for slope.

These obtained values of slope and intercept are used either alone or in combination to provide a calibration scale against which subsequent measurements are compared to obtain a measure of solute concentration.

The values of slope are negative as indicated by FIGS. 7 and 7A, and for 1% intralipid a value of $-1.56 \pm 0.037$ is given (FIG. 6). The units are $10^{-4}$ OD per 1 mM glucose per 1 cm separation. The error of the slope is 0.037, and thus, the signal-to-error ratio in the determination of 1 mM glucose would from these data appear to be approximately 50 at 1 cm separation and correspondingly less at ρ=7 cm. It is noted that the appropriate coefficient of Eqs. 6 and 7 involves the square root of concentration.

The sensitivity, however, varies with the scatterer concentration, and thus the experiment was repeated from 0.1%–1.5% of intralipid, and a new sensitivity constant, reduced to 1% scatterer concentration, is given in FIG. 6 (Table I) to be $1.56 \times 10^{-4}$ OD per 1 mM glucose per 1 cm separation per 1% intralipid. The square root relationship of Eqs. 6 and 7 is followed from 20 to 100 mM glucose, and the intercept follows a logarithmic relationship with a value of $90 \times 10^{-4}$ OD per cm per In 1 mM glucose. The values of the intercept increase with increasing intralipid $1.4 + 0.3 \times 10^{-4}$ OD/cm/1 mM glucose per intralipid %.

To monitor temperature variations, the vessel containing a solute (e.g., glucose) and scatterer (e.g., intralipid) is chilled to 20° C., and the temperature is slowly ramped to 35° C. by an electric hotplate (upon rapid stirring) and the optical effects are recorded. The scatterer is stirred by a magnetic bar, and the temperature is regulated by the heater/thermostat so that temperatures between 20 and 30° C. can be employed. The temperature of the system is measured by a mercury thermometer.

EXAMPLE 2

Male SD strain rats, weighing 250–300 g were used. After anesthetizing a rat by intraperitoneal injection pentobarbital (50 mg/kg weight), the liver was removed and perfused by Krebs-Ringer buffer containing 2 mM glucose. The buffer was oxygenated by the gas mixture 95% oxygen and 5% carbon dioxide. The liver was placed on an array of light sources and a detector with the separation of 1–3.3 cm. After liver perfusion became stable (20–30 minutes), the perfusate was changed to others containing different concentrations of glucose or mannitol. The oxygen concentration of outflow was simultaneously measured.

Precautions are necessary to ensure that the variations of the optical properties of the liver itself do not cause optical artifacts. Thus, the perfusion with solute is preceded and followed by control intervals. The lobes of the rat liver are laid upon an array of light sources and detectors similar to that indicated in FIGS. 1–1D, but with spacings of 1, 2 and 3 cm (and also 1.2, 1.5, and 2.2 cm) to account for the higher absorbance of the liver and the smaller size of the liver. Furthermore, the thickness of the lobe is approximately 2 cm and the tissue boundary conditions differ from the model of FIGS. 5 and 5A. We have chosen mannitol as the appropriate solute an contrasted to glucose in view of its negligible metabolic activity.

Figure 8:
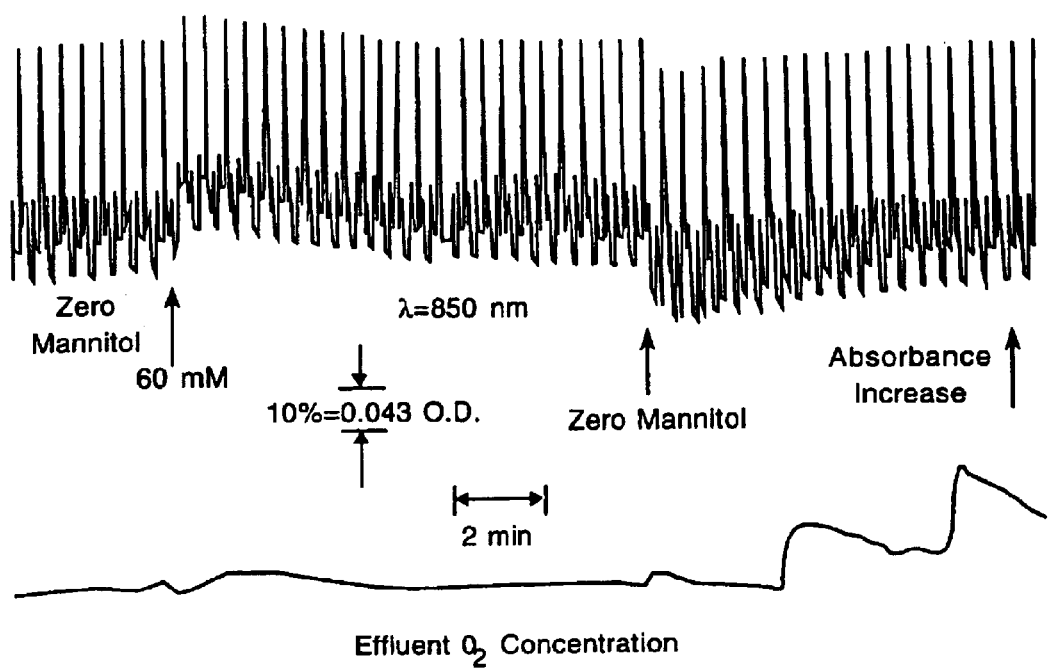
FIG. 8 is a schematic plot of the time course of a solute addition to the perfusate of rat liver.

A typical trace for the perfusion with 60 mM mannitol is shown in FIG. 8. The initial phase of absorbance increase is attributed to the entry of the mannitol into the sinusoids of the liver creating osmotic gradient, which equilibrates over the next 5 minutes. Thereafter, the absorbance change is assumed to be due to the equilibration of the mannitol with liver hepatocytes. In order to ensure that no remnant effect on the liver has occurred, the perfusate without solute is restored; the liver is reperfused with crystalloid in the absence of added mannitol. In this case, a decrease of absorbance occurs due to effusion of the mannitol from the tissue spaces, and thereafter the initial base line is restored. The mannitol effect is then measured as an early phase and a late phase, with respect to the two control levels.

Figure 8A:
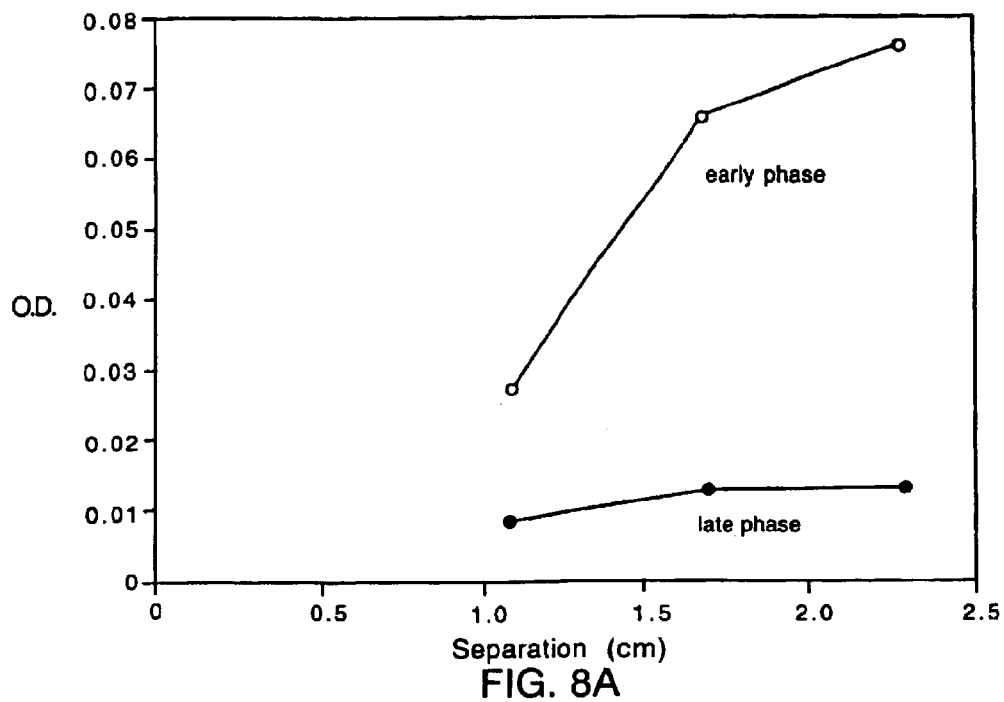
FIG. 8A is a plot of optical density (OD) as a function of input-output separation (ρ) illustrating the effect of mannitol upon the absorption of perfused liver (37° C.).
Figure 8B:
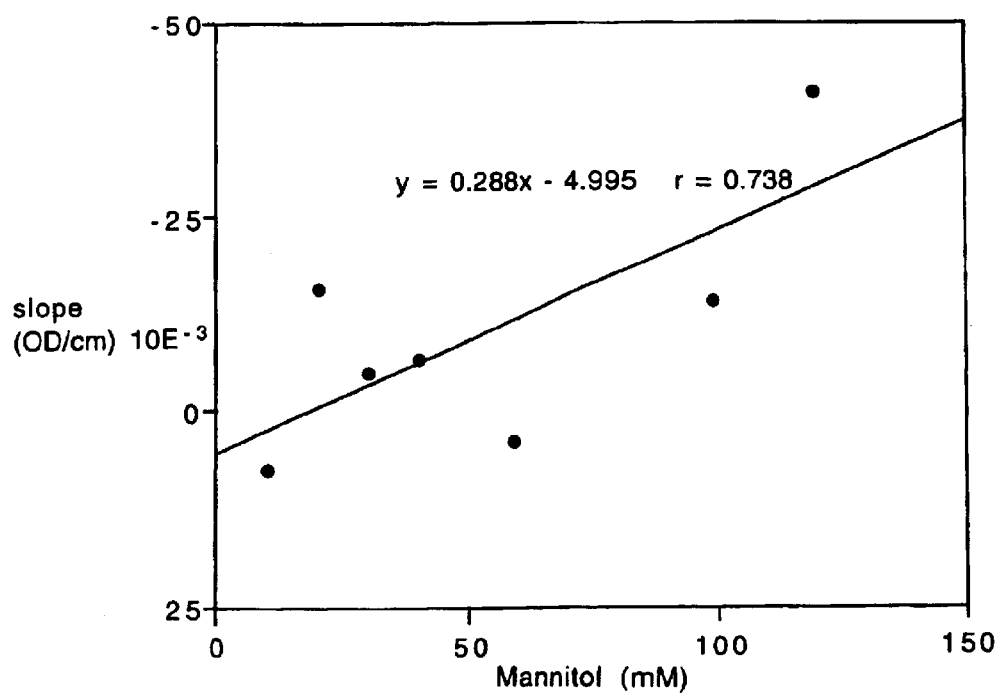
FIG. 8B is a plot of the slope of the OD plot of FIG. 8 as a function of mannitol concentration.

As shown in FIG. 8A, OD versus ρ plots are obtained. These are much "noisier" than the intralipid and yeast cell models, probably due to osmotic and perfusion pressure effects. First, the sign of the early and late phases is similar. The slope of the early phase corresponds to a $+18 \times 10^{-4}$ OD per one mM of mannitol per cm separation of input/output. The late phase corresponds to $_+1.7 \times 10^{-4}$ OD per mannitol per cm.

EXAMPLE 3

Changes in absorption, scattering coefficients, and optical pathlength due to the introduction of a solute in suspensions or in rat liver tissue were shown using time-domain, frequency-domain, and continuous-wave methods. These three methods measure optical properties of highly-scattering medium, transient response of mean pathlength change, and fast response to a change in optical properties and scattering changes, respectively. Wavelengths used were in the range of 780–850 nm.

In lipid or cell suspension measurements, a cylindrical container (17 cm diameter, 10 cm height) was filled with distilled water and various concentrations of a scattering medium. Intralipid (Kabi Pharmatica, Clayton, N. Dak.), with a 20% concentration, was diluted to 0.5–2.5% (vol/vol). In the case of cell suspensions, a slurry of either 1.4% or 2.8% by weight of baker's yeast in 20 mM phosphate buffer, pH 7, was added to the lipid solution. During measurements, optical properties (absorption, reduced scattering coefficients) were altered by titration of 50 mM of solutes such as glucose and mannitol. The light source and detector, connected to a NIR detection system such as those described above, were placed 3 cm above the suspension surface or from the side of the container.

Male SD strain rats (300–350 grams) were starved 24 hours to normalize liver physiological conditions. After anesthetizing each rat with a 50 mg/kg body weight intraperitoneal injection of pentobarbital, the rat liver was removed and perfused by Krebs-Ringer buffer (2 mM glucose, oxygenated by gas mixture of 95% oxygen and 5% carbon dioxide) until perfusion became stable (20–30 min.). The perfusate was switched between buffer and buffer solutions containing different concentrations of carbohydrates. The separation between light source and detector, which were attached to the major lobes of the liver, was 1.5 cm.

In simulations, equations (12) and (13) were used for the suspension and tissue cases, respectively, to calculate changes in reduced scattering coefficient under various conditions.

EXAMPLE 4

A non-invasive determination of potassium effusion within the brain of an (in vivo) animal model was demonstrated. The effusion of potassium from an hypoxic rat brain was measured as a light scattering change at 816 nm, a wavelength that is relatively indifferent to the oxygenation/deoxygenation of hemoglobin. The diagram FIG. 19 shows a calibration with a sucrose load in the brain which increased potassium ion concentration in the interstitial or extracellular space (and thus, light scattering). Injection of the anesthetic ketamine caused little light scattering change. When the rat was exposed to nitrogen gas (breathing), the initial scattering change is in the same direction as sucrose infusion, but was due to leakage of potassium from the neurons. Upon restoration of metabolic activity, a large overshoot appeared which subsided to baseline levels after several minutes. Light scattering was shown to demonstrate the functional state of the animal brain. Since photon migration in the human brain has been shown to be readily observable, the disclosed technique can be applied to patients who have conditions such as stroke, eschemia, head trauma, brain bleeds, coma, and other conditions known to those in the art to ascertain the general location of the injury (e.g., stroke) and the tissue volumes in which oxygen and hence energy is lacking. Correlation between the optical properties of tissue and tissue refractive index a) Simulation Results:

Based on equation (11), the dependence of reduced scattering coefficient, $\mu_s'$, of suspension models on the refractive index of scattering particles ($n_{in}$) and suspension fluid ($n_{ax}$) can be calculated assuming that the size and the volume fraction of the scattering particles do not change. FIG. 13(a) shows $\mu_s'$ values of a 0.5% Intralipid-glucose suspension as a function of added glucose concentration and corresponding refractive index of the lipid suspension, $n_{ax}$. The parameters used in this case are $a=0.25$ $\mu$m, $\phi=0.005$, $\lambda=800$ nm, $n_{in}=1.465$, and $n_{ax}=1.325+2.73\times10^{-5}\times[C]$, where [C] is the glucose concentration in MM (Maier et al. *Opt. Lett.* 19 (24), 2062–2064 (1994)). On the other hand, we use equation (12) to simulate $\mu_s'$ changes of a perfused rat liver as a function of added glucose concentration; the results are shown in FIG. 13(b). This calculation varies only the refractive index of the extracellular fluid as $n_{ax}=1.33+2.73\times10^{-5}\times[C]$ and keeps other parameters constant (a=10.68 µm, $\phi$=0.8, $\lambda$=800 nm, and $n_{in}$=1.465) (Beauvoit et al Biophys J. 67, 2501–2510 (1994)). The initial $\mu_s'$ value of 15.9 cm$^{-1}$ at 0 mM glucose concentration is based on a published, experimentally-measured data (1994). This dependence of $\mu_s'$ of the liver on the glucose concentration assumes that the liver cells are rigid. Both FIGS. 13(a) and 13(b) illustrate that if addition of glucose/carbohydrate in suspension models or in tissue, such as in perfused rat liver, does not change the size of the scatterers or cells, the reduced scattering coefficient, $\mu_s'$, of the corresponding system decreases as the added glucose concentration increases.

b) Experimental Results in Lipid and Cell Suspension Models:

FIG. 14 plots a set of time-domain experimental results of 0.5% Intralipid suspension as a function of nammitol concentration added into the suspension at a wavelength of 830 nm. By fitting the time-resolved spectroscopy data, we can obtain the values of mean optical pathlength, $\mu_s'$, and $\mu_a$, as plotted in FIGS. 14(a), 14(b), and 14(c), respectively. The solid data points in FIG. 14(a) were determined by substituting the measured reflectance into equation (13), whereas the dashed line with empty circles was calculated by replacing the fitted $\mu_a$ and $\mu_s'$ values in equation (14). The consistency between these two pathlength determinations confirms the correctness of the fitted values of $\mu_a$ and $\mu_s'$. FIGS. 14(a) and 14(b) clearly show that both the pathlength and the reduced scattering coefficient, $\mu_s'$, decrease as the mannitol concentration added in the suspension increases. FIG. 14(b) is in a good agreement with the simulation result shown in FIG. 13(a). FIG. 14(c) illustrates a very small decrease in $\mu_a$ value while the mannitol concentration becomes larger. Very similar results have been obtained for glucose titration (not shown) experiments.

We have also used the continuous-wave method to measure solute-induced changes of optical properties in lipid/cell suspensions. A variety of solutes (electrolytes, nonelectrolytes, sugars, and alcohols) has been studied, and some of the results have been reported (Chance et al. Anal. Biochem. 227, 351–362 (1995)). The results obtained with the continuous-wave method for the suspension models are very similar to those with the time-domain method and also similar to the theoretical calculations. An example, FIG. 15 shows a relationship of $\mu_s'/\mu_a$ versus mannitol concentration for an Intralipid-yeast suspension with mannitol titration.

Correlation Between the Optical Properties of Tissue and Tissue Cell Volume a) Simulation Results:

Since the cell volume fraction, $\phi$, is usually greater than 0.5 for tissues, equation (12) is used in this section. We consider three situations for the simulations: 1) changes in cell size only; 2) changes both in cell size and in refractive index of the extracellular fluid; and 3) changes in cell size, cell volume fraction, and refractive index of the extracellular fluid. The fact that introducing a carbohydrate into tissue, such as a perfused rat liver, causes cell shrinkage is considered in the simulations.

FIG. 16(a) shows the simulated dependence of $\mu_s'$ of a perfused rat liver on cell radius (top scale), with fixed parameters of cell volume fraction ($\phi$=0.8), intracellular ($n_{in}$=1,465), and extracellular ($n_{ax0}$=1.33) refractive indexes. The chosen value of $n_{in}$ is based on Refs. 5 and 26, and $n_{ax0}$ is extrapolated from Ref. 14. This calculation illustrates that a decrease only in tissue cell size results in an increase in reduced scattering coefficient, $\mu_s'$, and thus in pathlength; vice visa. A decrease in cell size may be caused by a temperature increase of tissue or by an addition of a carbohydrate in tissue. FIG. 16(a) also gives the dependence of $\mu_s'$ on glucose concentration (bottom scale) introduced into liver, having a relationship of a=$a_0$−k[C], where a is the cell radius, $a_0$=10.678 µm is the initial cell radius without any glucose addition, k=0.002 is a constant, and [C] is the glucose concentration. The k value corresponds to a factor that gives a decrease of 5% cell volume for each 100 mM glucose addition in liver.

A decrease in cell size can lead to a decrease in cell volume and thus in cell volume fraction, $\phi$, since $$\phi = \frac{V_{cell}}{V_{total}}.$$

Therefore, an addition of a carbohydrate to tissue can result in a decrease of $\phi$. This occurs when tissue cells shrink but the whole tissue volume does not change significantly. However, $\phi$ # can also remain constant when the addition of a carbohydrate to tissue results in water loss in the tissue, causing the total volume, $V_{total}$, to decrease. To simulate more realistically $\mu_s'$ change upon exposure to a carbohydrate, one considers an overall effect due to all changes in 1) cell size, 2) extracellular refractive index, and 3) cell volume fraction. The solid circles in FIG. 16(b) are calculated for the relationship between $\mu_s'$ and added glucose concentration with a variable cell radius, a , and a variable extracellular refractive index, $n_{ax}$, but a fixed cell volume fraction, $\phi$ (=0.8). On the other hand, the open circles in FIG. 16(b) correspond to the simulation of $\mu_s'$ for variable a, $n_{ax}$, and $\phi$ with a relationship of $$\phi = 4\pi \frac{a^3}{3} V_{total},$$

where $V_{total}$ remains constant. Except for $\phi$, other parameters for these two traces are the same, namely, $n_{in}$=1.465, $n_{ax}$=1.33+2.73×10$^{-5}$[C], a=10.678−2×10$^{-3}$[C] in µm, and $\lambda$=0.8 µm. These two circle traces show a contradictory behavior of $\mu_s'$ as the carbohydrate concentration increases. After considering all effects of cell size, extracellular refractive index, and cell volume fraction, we show from the simulation data that in the addition of a solute/carbohydrate in tissue, the overall scattering of tissue can increase or decrease depending on if $\phi$ decreases or is unchanged, respectively.

b) Experimental Results in a Perfused Rat Liver:

To separate the effects of changes in cell size and in extracellular refractive index on $\mu_s'$ due to a carbohydrate addition, temperature-dependent pathlength measurements were performed with the frequency-domain method (phase-modulation spectroscopy) for a perfused rat liver. In principle, if tissue temperature is lowered, K$^+$ inside tissue cells may come out from the cells, and extracellular water may enter the cells, leading to cell swelling. It is also known that the temperature effect on the refractive index of a scattering fluid is relatively small (1994), so changes in extracellular refractive index caused by temperature can be ignored. Then, the overall $\mu_s'$ value or optical pathlength of the swollen cells of a cooled tissue should decrease according to the simulation given in FIG. 16(a) above. On the other hand, if the cooled tissue is warming up, the cells will shrink, and the pathlength will increase accordingly. In the experiment, the temperature of the liver was altered by changing the temperature of the perfusate, which is contained in a thermally controlled bath. FIG. 17(a) corresponds to a cooling process of the liver from 37° C., the perfusate temperature measured in the bath, to 25° C. in about 10 minutes. A few (~2.5) minutes after the perfusate starts to cool down, the liver starts to response, and the pathlength keeps decreasing as the liver temperature goes down until the perfusate temperature stabilizes at the setting temperature of 25° C. In contrast, FIG. 17(b) shows an increase in pathlength when the perfusate of the perfused liver is warming up from 25° C. to 37° C. The time courses for the cooling down (FIG. 17(a)) and warming up (FIG. 17(b)) processes are not necessarily the same, mainly depending on the amount of cooling source (ice) and heating power used. FIG. 17 confirms the simulation results (FIG. 16(a)) that the scattering coefficient of the tissue, and thus corresponding optical pathlength measured, will increase/decrease with a decrease/increase in cell size.

To study coupled effects on $\mu_s'$ due to changes in both cell size and refractive index of the extracellular fluid, several carbohydrates were added in the perfusate for the liver perfusion experiments. FIG. 18 is a set of time-dependent curves of pathlength measurements with the frequency-domain method during the liver perfusion with three kinds of carbohydrates. Curves (a), (b), and (c) correspond to a perfusate containing 200 mM glucose, 200 mM mannitol, and 200 mM sucrose, respectively. Two traces in curve (b) represent two measurements of two individual livers, demonstrating that different livers may be under different physiological conditions and thus have different response rates to mannitol. FIG. 18 shows clearly that the pathlengths or the scattering properties are different in these three cases. The similarity between the glucose and mannitol perfusion is that the pathlength increases as the carbohydrate perfusion starts. But the pathlength in the glucose perfusion returns to its baseline much faster than that in the mannitol perfusion. In contrast to these two perfusions, the pathlength decreases when the sucrose perfusate enters the liver and does not return to its baseline until the sucrose starts washed out by the buffer. To quantify the values of $\mu_a$ and $\mu_s'$, the time-domain method was used for another sucrose perfusion, and the results are given in FIG. 19. It shows that the $\mu_s'$ values as well as optical pathlengths of the liver, perfused with 100 mM sucrose, decrease with a small variation of $\mu_a$ during perfusion. The agreement between the results obtained with the time- and frequency-domain methods confirms the correctness of the data.

The data given in FIGS. 13, 15, and 19 show a negligible change of $\mu_a$ and a consistent increase/decrease between $\mu_s'$ and pathlength due to an addition of a carbohydrate in the suspensions or tissue. These results are in good agreement with equation (15). Therefore, we can conclude that an increase/decrease of pathlength measured in tissue due to a carbohydrate addition reflects an increase/decrease of its overall scattering property.

The simulation and experimental results demonstrate that the reduced scattering coefficient of tissue can be affected largely by the changes in refractive index of the extracellular fluid and in cell volume caused by osmotic stress due to carbohydrate addition to the tissue. However, in the Intralipid-yeast suspension case (FIG. 15), it seems that the effect of yeast cell variation is not very notable since the result in this case is very similar to that of the pure lipid suspension. This can be explained by two reasons: 1) the cell volume fraction relative to the whole suspension volume is very small; 2) the yeast cells have polysaccharide walls, which are much more rigid than the regular membranes of tissue cells. Thus, the cell size and cell volume fraction of yeast cells would not change significantly by the osmotic pressure caused by the carbohydrate addition in the suspension.

Addition of a solute or carbohydrate into tissue can cause both a decrease in cell volume fraction and an increase in refractive index of the extracellular fluid. These two changes contradict each other in the overall scattering behavior of the tissue. So measurements of optical pathlength changes can show which factor, cell volume change or refractive index change, plays more important role than the other. In the liver glucose perfusion presented by curve (a) in FIG. 18, the pathlength of the perfused liver increases rapidly and then returns to its original value within 2–3 minutes. This pathlength variation indicates that a decrease in call size and in cell volume fraction, $\phi$, must occur in the beginning of the perfusion, but soon the shrunken cells regain some of their original volumes. When the washout buffer is switched on, the pathlength starts to decrease since in this case, the cells are under hypotonic condition so that they start to swell. Again, the pathlength returns to its baseline in 3 minutes when the cells recover their initial volumes. The data for mannitol perfusion shown by curve (b) in FIG. 18 are similar to those in the glucose perfusion except that the returning rate to the baseline for mannitol is slower than that for glucose. This can be explained by the smaller permeability of the liver cells to mannitol than to glucose, so the uptaking rate for mannitol is slower than that for glucose.

In principle, neither the Regulatory Volume Increase nor Decrease of tissue cells can regain the initial cell volume completely. It means that the pathlength given in curves (a) and (b) of FIG. 18 should not completely return to its initial value. However, the change in refractive index of the extracellular fluid also occurs and compensates the effect of the change of cell volume. Thus, the pathlength trace can stay about the baseline, return to the baseline, or go below the baseline, as demonstrated by the two traces in curve (b), after the initial prominent response, largely depending on the tissue type and conditions.

The pathlength data for the sucrose perfusion given by curve (c) in FIG. 18 is quite different from the other two cases in two aspects: 1) the pathlength decreases when the perfusion starts, and 2) the pathlength does not intend to return to its baseline until the washout buffer is switched on. It is known that 1) cell shrinkage occurs when the rat liver is perfused with sucrose (Haddad et al., *Am. J. Physiol.* 256, G563–G569 (1989), 2) the refractive index of sucrose is 1.34783, very similar to that of glucose (1.3479) (Windholz et al., *The Merck Index: An Encyclopedia of Chemicals, Drugs, and Biologicals*, Merck & Co., Inc., Rahway (1983), 3) the liver cell membrane is impermeable to sucrose (Haddad et al. (1989)). The first two points indicate that the effects caused by changes in cell size and extracellular refractive index in the sucrose and glucose perfusion of the liver should be very similar. An explanation for the opposition pathlength feature in the sucrose perfusion is that the cell volume fraction, $\phi$, remains unchanged in this case, behaving differently from that in the glucose perfusion. It has been reported that the liver perfused with sucrose was subjected to a large amount of water loss (Haddad et al. (1989)). Thus, it is possible that both $V_{cell}$, due to cell shrinkage, and $V_{total}$, due to water loss in tissue, decrease so that $\phi = V_{cell}/V_{total}$ remain constant. The impermeability of the liver cell membrane to sucrose can be taken to explain the non-return feature since in this case, only water movement from the intracellular to extracellular compartments is involved, preventing the Regulatory Volume Increase.

Detection in vivo of changes in scattering property owing to glucose intake on human subjects has been reported (Maier et al. (1994)). The measurements were performed on the thigh of the subject, and the scattering factor started to decrease a few minutes after the glucose ingestion, opposing to our results obtained in the liver glucose perfusion. This inconsistency may be due to the fact that the glucose in vivo measurement, performed on the human thigh, may include a large portion of muscle and blood, whereas the liver perfusion measurement only involves pure liver cells. Since muscle cells are absolutely non-spherical and very different from the liver cells in shape and composition, muscle cells may response to glucose quite differently from the liver cells. On the other hand, if the cell volume fraction does not change much by the glucose intake, the scattering factor will decrease mainly due to the change in extracellular refractive index. Also when blood is involved in the measurement, the coupling of uptaking process of glucose by the red blood cells and muscle cells complicates the mechanism of changes in scattering property.

These results successfully demonstrate using the NIR techniques for non-invasive physiological monitoring, such as monitoring tissue swelling by detecting pathlength (i.e., scattering property) change. For example, if the pathlength increases, the cells are shrinking. If additions of solutes/carbohydrates are involved, one may encounter multiple effects due to changes in cell size and in extracellular refractive index. But by using suitable carbohydrates, such as glucose or mannitol, effects of changes in cell size of tissue can dominate so that tissue swelling can still be detectable by monitoring the pathlength change.

In summary, the theoretical and experimental results show that addition of a solute/carbohydrate in tissue affects the size of tissue cells, the cell volume fraction, and the refractive index of the extracellular fluid, and thus affects the overall tissue scattering properties. The approximated approach of the Mie theory was used to calculate the effects of osmolarity and refractive index on reduced scattering coefficient of tissues and photon diffusion theory was used to associate the reduced scattering coefficient to the optical pathlength. Experimentally, all of the three NIR techniques are capable of measuring the changes of optical properties due to an addition of a solute in tissue models and in perfused rat livers. The temperature-dependent pathlength measurements of the perfused liver confirmed the dependence of tissue scattering on the tissue cell size. The liver results obtained with three kinds of carbohydrate perfusion display different scattering aspects which are explained by changes in call size and volume fraction.

FIG. 12 is a schematic diagram illustrating the difference in volume fraction of scattering particles between a scatterer suspension (a) and tissue or blood (b). In case (a), the volume fraction of the scatterers is $\phi=0.026$, whereas in case (b), the volume fraction of the scatterers is $\phi=0.73$.

FIG. 13 shows simulation results of the reduced scattering coefficient, $\mu_s'$, for a 0.5% Intralipid-glucose suspension (a) and a perfused liver (b). The calculation for (a) is based on equation (2), whereas the calculation for (b) is based on equation (3). The relationship between the glucose and refractive index for the scattering particle in the suspension or for the extracellular fluid of the tissue is given in the text. In case (b), the liver cells are assumed rigid; only the refractive index of the extracellular fluid varies.

FIG. 14 shows time-domain experimental results of a 0.5% Intralipid-mannitol suspension measured at 830 nm. This figure shows mean optical pathlength (a), reduced scattering coefficient $\mu_s'$ (b), and absorption coefficient $\mu_a$ (c) of the suspension as a function of mannitol concentration added in the suspension.

FIG. 15 shows experimental result, measured with the continuous-wave method, of a 0.5% Intralipid-yeast-mannitol suspension. It shows a decrease of the reduced scattering coefficient $\mu_s'$ (a) and a relative constant of the absorption coefficient $\mu_a$ (b) of the suspension with an increase in mannitol concentration in the suspension.

FIG. 16 shows the simulation results of the reduced scattering coefficient $\mu_s'$, for a perfused liver, based on equation (12), with more realistic conditions. FIG. 16(a) shows an increase of $\mu_s'$ with a decrease in size of the liver cells (top scale) or with an increase in glucose concentration (bottom scale) in the perfusate. In FIG. 16(a), the variable is only the cell radius; the extracellular refractive index and the cell volume fraction are both fixed. The solid circles in FIG. 16(b) were obtained by varying cell radius and extracellular refractive index. The open circles in FIG. 16(b) were calculated by varying cell radius, extracellular refractive index, and cell volume fration.

FIG. 17 shows temperature-dependent pathlength change of a perfused rat liver for a cooling process (a) and warming-up process (b). The data were obtained by the frequency-domain method.

FIG. 18 shows experimental results of pathlength changes of a perfused rat liver with 200 mM glucose (a), 200 mM mannitol (b), and 200 mM sucrose, respectively, in the perfusate. The two traces in case (b) were obtained from two different rat livers.

FIG. 19 shows experimental results of the absorption coefficient $\mu_a$ (a), the reduced scattering coefficient $\mu_s'$ (b), and mean optical pathlength (c) of a rat liver perfused with 100 mM sucrose. The data were determined by the time-resolved spectroscopy. The solid and empty circles correspond to the measurement at 780 nm and 830 nm, respectively.

Applications

Various solute concentrations may be monitored using the monitoring scheme of the present invention.

Example I

The present invention provides is simple, cost-effective, portable scheme for monitoring the concentration of sugars (mannitol, fructose, sucrose, glucose) in a patient. Sensitivities of $1\times10^{-4}$ $_\Delta$OD per mmol per percent intralipid at 25° C. have been observed. A comparison with a typical noise level of $10^{-5}$ $_\Delta$OD, suggests that the range of 8–12 mM can be detected satisfactorily.

The glucose concentration in a patient is monitoring according to this example by attaching the monitor of FIGS. 1–1D to the patient on the breast, the belly, the finger, or on the head. The optimum tissue for this determination is one in which the extravascular glucose level is rapidly equilibrated with the blood vessels.

Figure 9:
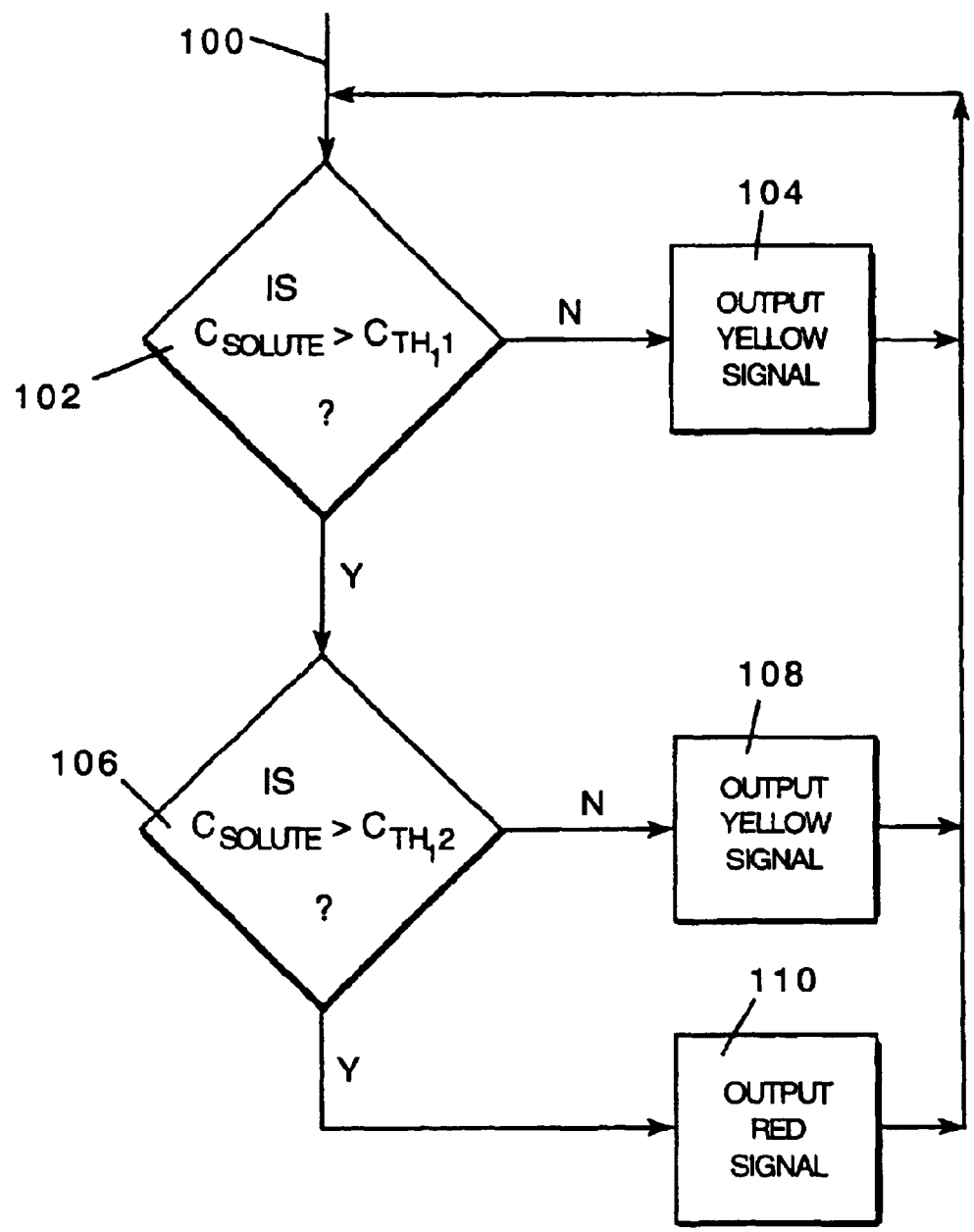
FIG. 9 is a flow diagram of a scheme for indicating to a patient measured solute concentration.

Referring to FIG. 9, in one preferred embodiment of a glucose monitor useful, e.g., for monitoring the glucose level of a diabetic patient, the patient's blood glucose concentration is detected using the process described above in connection with FIG. 4 (100). In one embodiment, the patient reads the extrapolated slope and intercept values directly from the output of a comparator (e.g., a computer or other processor) and compares these values to a predetermined calibration scale (described above).

In an alternative embodiment, a processor receives the extrapolated slope and intercept values and compares these values to a predetermined stored calibration scale. The processor further implements the following steps to indicate to the patient the measured solute concentration. If the measured concentration ($C_{solute}$) is less than a first predetermined threshold concentration ($C_{th,1}$), e.g., 0–100 mMol and more preferably 50 mmol (step 102), a green signal is output (104), e.g., by lighting a green light, indicating the patient's blood glucose level is generally within normal levels. If the measured concentration is greater than $C_{th,1}$, the measured concentration is compared against a second predetermined threshold concentration ($C_{th,2}$), e g., 50–200 mMol and more preferably 120 mmol (step 106). If $C_{solute}$ is less than this second threshold concentration, a yellow signal is output (108), indicating that the patient's blood glucose level has risen above normal levels and should be monitored carefully. If $C_{solute}$ is greater than $C_{th,2}$, a red signal is output (110), indicating that the patient should attempt to remedy his or her condition.

Example II

The alcohol concentration in a patient may also be monitored using the scheme according to the present invention. Ethanol readily equilibrates with tissue spaces and gives a relatively small but significant signal. Accordingly, a patient (as used herein the term "patient" is used to broadly refer to a person in general whether or not the person is being treated for a medical problem) attaches the monitor of FIGS. 1–1D to the breast, the belly, the finger, or the head. A processor, as described above in connection with Example I receives as input light intensity signals from a monitor as described in connection with FIGS. 1–1D and implements the algorithms shown in FIGS. 4 and 9 to provide a measure of the alcohol content in the patient's system.

The calibration scales are determined empirically as described above, e.g., in connection with Example 1. The threshold levels ($C_{th,1}$, $C_{th,2}$) are selected to correspond to desired criteria (e.g., legal drinking limit).

Example III

The concentration of salts (e.g., NaCl, KCl and MOPS) in a patient may also be monitored using the scheme according to the present invention. Accordingly, a patient attaches the monitor of FIGS. 1–1D to the breast, the belly, the finger, or the head. A processor, as described above in connection with Example I receives as input light intensity signals from a monitor as described in connection with FIGS. 1–1D and implements the algorithms shown in FIGS. 4 and 9 to provide a measure of the alcohol content in the patient's system. FIG. 10 (Table II) includes data on NaCl, KCl, and MOPS. The effect of these electrolytes is relatively small but significant.

The calibration scales are determined empirically as described above, e.g., in connection with Example 1. The threshold levels ($C_{th,1}$, $C_{th,2}$) are selected to correspond to desired criteria, depending, e.g., on the health of the patient. For example, patient's with high blood pressure would be assigned lower threshold concentrations.

Example IV

Enhanced results are achievable if the effects of solute concentrations other than that which is to be measured can be ignored. According to this example, the history of the patient is well characterized so that it can be assumed that variations in the monitored concentration level are due to variations in the solute concentration that is desired to be measured.

For example, an enhanced glucose concentration measurement of a patient is obtained using the monitor described in FIGS. 1–1D, which is coupled to a processor for implementing the steps of FIG. 4, when the patient has not subjected himself or herself to elevated concentrations of other scattering solutes, such as alcohol and salts.

In view of the low specificity in solute discrimination, especially the physiologically important ones, glucose, ethanol, mannitol, and to a lesser extent NaCl and KCl, the in vivo studies are undertaken with supplementary information of the parenteral fluids in use. In addition, the osmotic transients and indeed the osmotic state of the tissue can be of importance, especially in patients undergoing dialysis procedures. Finally, and possibly most important, is the body tissue temperature, which should be monitored in the particular tissue volume studies optically, probably by the water absorption.

FIG. 11 (Table III) illustrates the effect of a variety of solutes, mannitol, fructose, and propanediol in the range of molarities up to that indicated in the table. The slope is normalized in the same way as above, except it is not divided by the percent of intralipid. The slope values are within the experimental error equal to mannitol and fructose. Alcohols and propanediol give a significantly smaller slope per mM and a much smaller intercept after connection for dilution (see below). The small effect of methanol on yeast cells as a scatterer is noted in Table IV.

At the same time, an appropriate correction for water absorption may be implemented.

Furthermore, since intensity measurements are especially sensitive to changes in the skin contact between the probe and the phantom or the probe and the body tissue makes measurements which do not depend upon intensities vastly preferable, and one of these methods is the phase modulation system, which surely would be the ultimate system for most reliable measurements. However, the relationship between the intensity signal and the phase signal is such that very high phase sensitivities are required. The absorbance limitation of $10^{-5}$ may have to be measured, which requires similar accuracies of phase determination.

Other Embodiments

More than three sources may be used to obtain enhanced measurements by obtaining a greater number of data points from which to extract the linear parameters (slope and intercept).

Instead of using multiple light sources a single source may be used, which applies the light to the biological system from locations spaced from the detector by different distances. Alternatively, the single source may remain stationary and the detector may be sequentially moved to detecting positions located at different distances from the source.

The monitoring scheme described herein has a relatively small wavelength dependence. Thus, a dual wavelength method may be used for this purpose for the minimization of hemoglobin crosstalk. In this technique the hemoglobin concentration is quantified by an appropriate phase modulation spectrophotometer to provide accurate path length information at the wavelengths involved. Thus, the discrepancy of absorbance measurements at 850 nm from the hemoglobin spectrum can be assumed to be counted as pertaining to the solute measurement.

Possible variability of the light entry into the tissue and its arrival at the detector system consisting of a silicon diode or a fiber coupler (e.g., due to variable tissue contact) may be compensated for by frequency-domain methods, which may have a significant advantage for tissue contact. The use of several input-output spacings is necessary for these determinations. The different spacings sample different tissue volumes of different depths: the short spacing—shallow and the long spacing—deep tissue volumes. Thus, in cases where heterogeneous tissue is involved, the possibility that different solute levels are sampled at different input-output spacings should be compensated for.

Time-domain methods may alternatively be used. These methods sample different tissue volumes for the calculation $\mu_s'$ and $\mu_a$ (early and late, respectively). The use of Fourier transformation from time to frequency domain may rectify this problem. In these frequency-domain devices, the high frequency waves penetrate shallowly and the low frequency deeply. Thus, dual measurements, particularly at a pair of wavelengths at which the absorption is canceled out, serve as useful means for calculating scattering factor.

Still other embodiments are within the scope of the invention. The above solutes can be monitored or their concentration can be measured by a time resolved spectroscopy (TRS) or a phase modulation spectroscopy (PMS). Suitable TRS systems are described in U.S. Pat. Nos. 5,119,815 or 5,386,827, which are both herein incorporated by reference. The TRS system employs one or more visible or infrared wavelengths sensitive (i.e., due to variation in absorption or scattering) to the measured solute directly or indirectly. The TRS system measures in vivo the values of the effective scattering coefficient ($\mu_s'$) or the absorption coefficient ($\mu_a$) and correlates these values to a concentration of the solute.

Alternatively, the measurements are performed using a PMS system described in U.S. Pat. Nos. 4,972,331, 5,122,974 or 5,187,672, or in International Applications PCT/US94/02764, filed Mar. 15, 1993, or PCT/US92/00463, filed Jan. 21, 1992, all of which are incorporated by reference. The PMS system employs light of one or more

What is claimed is:

1. A system for in vivo characterization of biological tissue by measuring scattering properties of the tissue, comprising:
   a source-detector arrangement including at least one light source constructed to deliver into biological tissue light of at least one wavelength, at a known location, and at least one light detector constructed to provide at least one detected signal, wherein said detected signal depends on photon migration paths in the examined biological tissue;
   an oscillator constructed to generate a first carrier waveform at a frequency on the order of $10^8$ Hz, wherein said light source is coupled to said oscillator and constructed to generate light modulated by said carrier waveform; said detector being constructed to detect said modulated light that has migrated in the tissue;
   a phase detector constructed to measure a phase shift of said detected light that has migrated in the tissue compared to said introduced light and provide said phase shift signal to said processor; and
   a processor arranged to determine, based on said detected light and said phase shift signal, scattering properties of the biological tissue.

2. The system of claim 1 wherein said processor is further arranged to calculate a scattering coefficient.

3. The system of claim 1 wherein said light source is arranged to deliver said light of said wavelength directly to the skin for in vivo examination of the biological tissue.

4. The system of claim 1 wherein said light detector is arranged to detect said light emitted from the biological tissue through the skin for in vivo examination of the biological tissue.

5. The system of claim 1 wherein said source-detector arrangement is constructed to change said photon migration paths in the examined tissue.

6. The system of claim 1 wherein said source-detector arrangement is constructed to deliver said light of said wavelength being selected with respect to a solute.

7. The system of claim 6 wherein said processor is further arranged to calculate concentration of said solute.

8. The system of claim 1 wherein said source-detector arrangement is constructed to deliver said light of said wavelength being selected with respect to an exogenous contrast agent bonded to a solute.

9. The system of claim 8 wherein said processor is further arranged to calculate concentration of said solute.

10. The system of claim 1 wherein said source-detector arrangement is constructed to deliver said light of said wavelength being selected with respect to one of the following: a low molecular weight carbohydrate, an alcohol, or an electrolyte.

11. The system of claim 1 wherein said source-detector arrangement is constructed to deliver said light of said wavelength being selected with respect to one of the following: mannitol, fructose, sucrose, glucose, propanediol, methanol, ethanol, sodium ion, potassium ion, and chloride ion.

12. The system of claim 1 wherein said source-detector arrangement is constructed to deliver said light to one of the following: the finger, the arm, the head, the belly, and the liver.

13. A system for in vivo characterization of biological tissue by measuring scattering properties of the tissue, comprising:
   a source-detector arrangement including at least one light source constructed to deliver into biological tissue light of at least one wavelength, at a known location, and at least one light detector constructed to provide at least one detected signal, wherein said detected signal depends on photon migration paths in the examined biological tissue;
   a pulsar constructed to generate pulses of an input waveform of duration on the order of a nanosecond or less, wherein said light source, receiving said pulses of said input waveform, is constructed to introduce into the biological tissue pulses of said at least one wavelength having said input waveform; and said detector constructed to detect over time a pulse waveform;
   an analyzer, connected to said processor, constructed to store over time signals corresponding to said detected pulse waveforms; and
   a processor constructed to determine changes in shapes of said detected pulse waveforms relative to said input pulse waveform, and based upon said changes determine said scattering properties of the biological tissue.

14. The system of claim 13 wherein said processor is further arranged to calculate a scattering coefficient.

15. The system of claim 13 wherein said light source is arranged to deliver said light of said wavelength directly to the skin for in vivo examination of the biological tissue.

16. The system of claim 13 wherein said light detector is arranged to detect said light emitted from the biological tissue through the skin for in vivo examination of the biological tissue.

17. The system of claim 13 wherein said source-detector arrangement is constructed to change said photon migration paths in the examined tissue.

18. The system of claim 13 wherein said source-detector arrangement is constructed to deliver said light of said wavelength being selected with respect to a solute.

19. The system of claim 18 wherein said processor is further arranged to calculate concentration of said solute.

20. The system of claim 13 wherein said source-detector arrangement is constructed to deliver said light of said wavelength being selected with respect to an exogenous contrast agent bonded to a solute.

21. The system of claim 20 wherein said processor is further arranged to calculate concentration of said solute.

22. The system of claim 13 wherein said source-detector arrangement is constructed to deliver said light of said wavelength being selected with respect to one of the following: a low molecular weight carbohydrate, an alcohol, or an electrolyte.

23. The system of claim 13 wherein said source-detector arrangement is constructed to deliver said light of said wavelength being selected with respect to one of the following: mannitol, fructose, sucrose, glucose, propanediol, methanol, ethanol, sodium ion, potassium ion, and chloride ion.

24. The system of claim 13 wherein said source-detector arrangement is constructed to deliver said light to one of the following: the finger, the arm, the head, the belly, and the liver.

* * * * *